US010098353B2

(12) United States Patent
Breakfield et al.

(10) Patent No.: US 10,098,353 B2
(45) Date of Patent: Oct. 16, 2018

(54) METHODS AND COMPOSITIONS FOR CONTROLLING ROOT KNOT NEMATODES

(71) Applicant: NewLeaf Symbiotics, Inc., St. Louis, MO (US)

(72) Inventors: Natalie Breakfield, St. Louis, MO (US); Gregg Bogosian, St. Louis, MO (US)

(73) Assignee: NEWLEAF SYMBIOTICS, INC., St. Louis, MO (US)

(*) Notice: Subject to any disclaimer, the term of this patent is extended or adjusted under 35 U.S.C. 154(b) by 0 days.

(21) Appl. No.: 15/352,016

(22) Filed: Nov. 15, 2016

(65) Prior Publication Data
US 2017/0135352 A1 May 18, 2017

Related U.S. Application Data

(60) Provisional application No. 62/257,309, filed on Nov. 19, 2015, provisional application No. 62/255,882, filed on Nov. 16, 2015.

(51) Int. Cl.
A01N 63/00 (2006.01)

(52) U.S. Cl.
CPC .................. A01N 63/00 (2013.01)

(58) Field of Classification Search
CPC .................................. A01N 63/00
See application file for complete search history.

(56) References Cited

U.S. PATENT DOCUMENTS

| 3,911,118 | A | * | 10/1975 | O'Melia | C07F 9/585 |
| | | | | | 514/89 |
| 5,106,648 | A | | 4/1992 | Williams | |
| 5,512,069 | A | | 4/1996 | Holland et al. | |
| 5,961,687 | A | | 10/1999 | Joshi et al. | |
| 6,174,837 | B1 | | 1/2001 | Joshi et al. | |
| 6,329,320 | B1 | | 12/2001 | Joshi et al. | |
| 7,435,878 | B2 | | 10/2008 | Holland | |
| 8,153,118 | B2 | | 4/2012 | Holland et al. | |
| 8,181,388 | B2 | | 5/2012 | Berger | |
| 9,181,541 | B2 | | 11/2015 | Bogosian | |
| 9,845,462 | B2 | | 12/2017 | Bogosian | |
| 2001/0001095 | A1 | | 5/2001 | Joshi et al. | |
| 2015/0337256 | A1 | | 11/2015 | Bogosian | |
| 2016/0046925 | A1 | | 2/2016 | Bogosian | |
| 2016/0073641 | A1 | | 3/2016 | Allen et al. | |
| 2016/0120188 | A1 | | 5/2016 | Bogosian | |
| 2016/0295868 | A1 | | 10/2016 | Jones et al. | |
| 2016/0302423 | A1 | | 10/2016 | Jones et al. | |
| 2016/0302424 | A1 | | 10/2016 | DiDonato et al. | |
| 2016/0302425 | A1 | | 10/2016 | DiDonato et al. | |
| 2017/0086464 | A1 | | 3/2017 | Floro et al. | |
| 2017/0164618 | A1 | | 6/2017 | Breakfield et al. | |
| 2017/0238553 | A1 | | 8/2017 | Jones et al. | |

FOREIGN PATENT DOCUMENTS

| WO | 2012/140212 A2 | 10/2012 |
| WO | 2013/181610 A1 | 12/2013 |
| WO | 2014194189 A1 | 12/2014 |
| WO | 2015/085063 A1 | 6/2015 |
| WO | 2015142393 A1 | 9/2015 |
| WO | 2016069564 A1 | 5/2016 |
| WO | 2016201284 A2 | 12/2016 |

OTHER PUBLICATIONS

Vetrivelkalia, P., Biocontrol Potential of Endophytic bacteria on Meloidogyne incognita and its effect on Plant Growth in Bhendi, 2010, Journal of Biopesticides, vol. 3, Issue 3, pp. 452-457.*
Prabhu, S., Suppresive Effect of Methylobacterium fujisawaenese Against Root-Knot Nematode, Meloidogyne incognita, 2009, Indian Journal of Nematology, Vo. 39, No. 2, pp. 165-169.*
"ATCC Bacteria and Bacteriophages", American Type Culture Collection, 1996, pp. 213-214, 19th Edition.
"ATCC Preservation Methods: Freezing and Freeze-Drying", 1991, pp. 5-13, 2nd Edition, ATCC.
Abanda-Nkpwatt et al., "Molecular Interaction Between Methylobacterium Extorquens and Seedlings: Growth Promotion, Methanol Consumption, and Localization of the Methanol Emission Site", Journal of Experimental Botany, Oct. 16, 2006, vol. 57 No. 15, pp. 4025-4032.
Corpe et al., "Ecology of the Methylotrophic Bacteria on Living Leaf Surfaces", FEMS Microbiology Ecology, 1989, vol. 62, pp. 243-250.
Green, "Methylobacterium", Prokaryotes, 2006, vol. 5, Chapter 3.1.13, pp. 257-265.
Holland, "Methylobacterium and Plants", Recent Research Developments in Plant Physiology, 1997, pp. 207-213, vol. 1.
Joe et al., "Development of Alginate-Based Aggregate Inoculants of Methylobacterium sp. and Azospirillum Brasilence Tested Under In Vitro Conditions to Promote Plant Growth", Journal of Applied Microbiology, Nov. 22, 2013, pp. 408-423, vol. 116, Issue 2.
Lidstrom et al., "Plants in the Pink: Cytokinin Production by Methylbacterium", Journal of Bacteriology, Apr. 2002, p. 1818, vol. 184, No. 7.
Madhaiyan et al., "Growth promotion and induction of systemic resistance in rice cultivar Co-47 (Oryza sativa L.) by Methylobacterium spp.", Biology and Fertility of Soils, 2005, pp. 350-358, vol. 41.
Madhaiyan et al., "Metal Tolerating Methylotrophic Bacteria Reduces Nickel and Cadmium Toxicity and Promotes Plant Growth of Tomato (Lycopersicon esculentum L.)", Chemosphere, May 23, 2007, pp. 220-228, vol. 69.
Madhaiyan et al., "Pink-Pigmented Facultative Methylotrophic Bacteria Accelerate Germination, Growth and Yield of Sugarcane Clone Co86032 (Saccharum officinarum L.)", Biology and Fertility of Soils, 2005, pp. 350-358, vol. 41.

(Continued)

Primary Examiner — Sue X Liu
Assistant Examiner — Andriae M Holt
(74) Attorney, Agent, or Firm — Thompson Coburn LLP; Charles P. Romano

(57) ABSTRACT

The present disclosure provides compositions comprising Root-Knot Nematode (RKN)-active Methylobacterium sp., methods for controlling RKN infections of plants, and methods of making the compositions.

16 Claims, No Drawings
Specification includes a Sequence Listing.

(56) References Cited

OTHER PUBLICATIONS

Omer et al., "Plant Colonization by Pink-Pigmented Facultative Methylotrophic Bacteria (PPFMs)", FEMS Microbiology Ecology, Mar. 2004, pp. 319-326, vol. 47 No. 3.
Rastogi et al., "Leaf Microbiota in an Agroecosystem Spatiotemporal Variation in Bacterial Community Composition on Field-Grown Lettuce", The ISME Journal, Apr. 26, 2012. pp. 1812-1822, vol. 6.
Sy, A. et al., "Methylotrophic Metabolism Is Advantageous for Methylobacterium extorquens during Colonization of Medicago truncatula under Competitive Conditions", Applied and Environmental Microbiology, 2005, pp. 7245-7252, vol. 71, No. 11.
Vaidehi et al., "Adhesion of Methylobacterium Cells to Rice Roots: Active Metabolism of Miropartner Determines the Degree of Adsorption Level at Rhizosphere", International Journal of Research in Pure and Applied Microbiology, 2012, pp. 54-58, vol. 2, No. 4.
Wessman et al., "Impact of Matrix Properties on the Survival of Freeze-Dried Bacteria", Journal of the Science and Food Agriculture, 2011, pp. 2518-2528, vol. 91.

* cited by examiner

SEQUENCE LISTING

<160> NUMBER OF SEQ ID NOS: 1

<210> SEQ ID NO 1
<211> LENGTH: 1473
<212> TYPE: DNA
<213> ORGANISM: Methylobacterium sp.

<400> SEQUENCE: 1

```
ggtgatccag ccgcaggttc ccctacggct accttgttac gacttcaccc cagtcgctga      60
ccctaccgtg gtcgcctgcc tccttgcggt tggcgcagcg ccgtcgggta agaccaactc     120
ccatggtgtg acgggcggtg tgtacaaggc ccgggaacgt attcaccgtg gcatgctgat     180
ccacgattac tagcgattcc gccttcatgc acccgagttg cagagtgcaa tccgaactga     240
gacggctttt ggggatttgc tccaggtcgc cccttcgcgt cccactgtca ccgccattgt     300
agcacgtgtg tagcccatcc cgtaagggcc atgaggactt gacgtcatcc acaccttcct     360
cgcggcttat caccggcagt ctccctagag tgcccaactg aatgatggca actaaggacg     420
tgggttgcgc tcgttgcggg acttaaccca acatctcacg acacgagctg acgacagcca     480
tgcagcacct gtgtgcgcgc ctccgaagag gactgggaat ctctcccat aacacgccat     540 gtcaaaggat ggtaaggttc tgcgcgttgc ttcgaattaa accacatgct ccaccgcttg     600
tgcgggcccc cgtcaattcc tttgagtttt aatcttgcga ccgtactccc caggcggaat     660
gctcaaagcg ttagctgcgc tactgaggtg caagcacccc aacagctggc attcatcgtt     720
tacggcgtgg actaccaggg tatctaatcc tgtttgctcc ccacgctttc gcgcctcagc     780
gtcagtaatg gtccagttgg ccgccttcgc caccggtgtt cttgcgaata tctacgaatt     840
tcacctctac actcgcagtt ccaccaacct ctaccatact caagcgtccc agtatcgaag     900
gccattctgt ggttgagcca caggctttca ccccgactt aaaacgccgc ctacgcgccc     960
tttacgccca gtgattccga gcaacgctag ccccttcgt attaccgcgg ctgctggcac    1020
gaagttagcc ggggcttatt cctccggtac cgtcattatc gtcccggata aaagagcttt    1080
```

-continued

```
acaaccctaa ggccttcatc actcacgcgg catggctgga tcaggcttgc gcccattgtc    1140
caatattccc cactgctgcc tcccgtagga gtctgggccg tgtctcagtc ccagtgtggc    1200
tgatcatcct ctcagaccag ctactgatcg tcgccttggt gagccgttac ctcaccaact    1260
agctaatcag acgcgggccg atcctccggc agcaagcctt tccccaaaag ggcgtatccg    1320
gtattagctc aagtttccct gagttattcc gaaccagagg gcacgttccc acgcgttact    1380
cacccgtccg ccgctgacac ccgaaagtgc ccgctcgact tgcatgtgtt aagcctgccg    1440
ccagcgttcg ctctgagcca ggatcaaact ctc                                 1473
```

METHODS AND COMPOSITIONS FOR CONTROLLING ROOT KNOT NEMATODES

CROSS-REFERENCE TO RELATED APPLICATIONS

This U.S. Non-Provisional Patent Application claims the benefit of U.S. Provisional Patent Application No. 62/257,309, filed Nov. 19, 2015 and incorporated herein by reference in its entirety, and the benefit of U.S. Provisional Patent Application No. 62/255,882, filed Nov. 16, 2015 and incorporated herein by reference in its entirety.

SEQUENCE LISTING STATEMENT

A sequence listing containing the file named 53907_160556 Seq List_ST25.txt which is 2384 bytes (measured in MS-Windows®) and created on Nov. 15, 2016, comprises 1 sequence, is provided herewith via the USPTO's EFS system, and is incorporated herein by reference in its entirety.

BACKGROUND

One-carbon organic compounds such as methane and methanol are found extensively in nature, and are utilized as carbon sources by bacteria classified as methanotrophs and methylotrophs. Methanotrophic bacteria include species in the genera *Methylobacter*, *Methylomonas*, *Methylomicrobium*, *Methylococcus*, *Methylosinus*, *Methylocystis*, *Methylosphaera*, *Methylocaldum*, and *Methylocella* (Lidstrom, 2006). Methanotrophs possess the enzyme methane monooxygenase, that incorporates an atom of oxygen from $O_2$ into methane, forming methanol. All methanotrophs are obligate one-carbon utilizers that are unable to use compounds containing carbon-carbon bonds. Methylotrophs, on the other hand, can also utilize more complex organic compounds, such as organic acids, higher alcohols, sugars, and the like. Thus, methylotrophic bacteria are facultative methylotrophs. Methylotrophic bacteria include species in the genera *Methylobacterium*, *Hyphomicrobium*, *Methylophilus*, *Methylobacillus*, *Methylophaga*, *Aminobacter*, *Methylorhabdus*, *Methylopila*, *Methylosulfonomonas*, *Marinosulfonomonas*, *Paracoccus*, *Xanthobacter*, *Ancylobacter* (also known as *Microcyclus*), *Thiobacillus*, *Rhodopseudomonas*, *Rhodobacter*, *Acetobacter*, *Bacillus*, *Mycobacterium*, *Arthobacter*, and *Nocardia* (Lidstrom, 2006).

Most methylotrophic bacteria of the genus *Methylobacterium* are pink-pigmented. They are conventionally referred to as PPFM bacteria, being pink-pigmented facultative methylotrophs. Green (2005, 2006) identified twelve validated species in the genus *Methylobacterium*, specifically *M. aminovorans*, *M. chloromethanicum*, *M. dichloromethanicum*, *M. extorquens*, *M. fujisawaense*, *M. mesophilicum*, *M. organophilum*, *M. radiotolerans*, *M. rhodesianum*, *M. rhodinum*, *M. thiocyanatum*, and *M. zatmanii*. However, *M. nidulans* is a nitrogen-fixing *Methylobacterium* that is not a PPFM (Sy et al., 2001). *Methylobacterium* are ubiquitous in nature, being found in soil, dust, fresh water, sediments, and leaf surfaces, as well as in industrial and clinical environments (Green, 2006).

SUMMARY

Provided herein are isolated RKN-active *Methylobacterium* sp., compositions comprising RKN-active *Methylobacterium* sp., methods of using the compositions to control RKN damage to plants, plant parts, and plants derived therefrom, and methods of making the compositions. Such RKN-active *Methylobacterium* sp. are in certain instances referred to herein as simply "*Methylobacterium*" or as "PPFM" (pink-pigmented facultative methylotrophs). In certain embodiments, the RKN-active *Methylobacterium* sp. is a *Methylobacterium* isolate selected from the group consisting of *Methylobacterium* NLS0037, a derivative thereof, and a NLS0037-related *Methylobacterium*. In certain embodiments, the RKN-active *Methylobacterium* sp. is NLS0037, a derivative thereof, and a NLS0037-related *Methylobacterium*.

Methods for reducing *Meloidogyne* sp. damage to a plant that comprise applying a composition comprising a *Methylobacterium* selected from the group consisting of *Methylobacterium* NLS0037 (NRRL B-50941), a derivative thereof, and a NLS0037-related *Methylobacterium* and an agriculturally acceptable excipient and/or an agriculturally acceptable adjuvant to a plant part to obtain a treated plant part; and growing the plant from said treated plant part in the presence of *Meloidogyne* sp., wherein *Meloidogyne* sp. damage to the plant is reduced in comparison to a control plant from a control plant part that is not treated with the *Methylobacterium* and that is grown in the presence of *Meloidogyne* sp. are provided. In certain embodiments, the *Methylobacterium* is present on said treated plant part in an amount of at least about $1 \times 10^2$ or $1 \times 10^3$ colony forming units (CFU) of said *Methylobacterium* per treated plant part. In certain embodiments, about $1 \times 10^2$, $1 \times 10^3$, or $1 \times 10^4$ CFU to about $1 \times 10^8$ or $1 \times 10^9$ CFU of the RKN-active *Methylobacterium* sp. are provided on a 100 mm$^2$ surface of a treated plant part. In certain embodiments of the methods, the composition comprises a solid substance with adherent RKN-active *Methylobacterium* grown thereon or an emulsion having RKN-active *Methylobacterium* grown therein. In certain embodiments of the methods, the composition comprises the RKN-active *Methylobacterium* sp. at a titer of about $1 \times 10^4$ or $1 \times 10^5$ colony-forming units per ml to about $1 \times 10^9$, $1 \times 10^{10}$, $6 \times 10^{10}$, $1 \times 10^{11}$, $5 \times 10^{11}$, or $1 \times 10^{12}$ colony-forming units of *Methylobacterium* per mL of a liquid or emulsion. In certain embodiments of the methods, the composition comprises the RKN-active *Methylobacterium* sp. at a titer of about $5 \times 10^8$, $1 \times 10^9$, or $1 \times 10^{10}$ colony-forming units per gram (CFU/gm) to about $1 \times 10^{12}$ or $5 \times 10^{13}$ colony-forming units of *Methylobacterium* per gram of a solid substance to which the *Methylobacterium* is adhered or at a titer of about $1 \times 10^6$ CFU/mL to about $1 \times 10^9$ CFU/mL of the *Methylobacterium* in an emulsion. In certain embodiments, the NLS0037 derivative is obtained by mutagenizing or transforming *Methylobacterium* NLS0037. In certain embodiments, the NLS0037-related *Methylobacterium* is characterized by having a gene encoding a 16S RNA that has at least 95%, 96%, 97%, 98%, 99%, 99.5%, 99.7%, 99.9%, or 100% sequence identity across the entire length of SEQ ID NO: 1. In certain embodiments of any of the aforementioned methods, the *Methylobacterium* is heterologous to the plant part. In certain embodiments of any of the aforementioned methods, the *Methylobacterium* is *Methylobacterium* NLS0037 (NRRL B-50941) and the plant part is not a tomato plant part. In certain embodiments of any of the aforementioned methods, the *Meloidogyne* sp. damage is selected from the group consisting of a reduction in plant growth, yield, water-deficit tolerance, chlorosis, produce quality, and combinations thereof. In certain embodiments of the aforementioned method, the reduction in produce quality is evidenced by a decrease in the number of galls or egg masses in produce obtained from the plant in comparison to the number of galls or egg masses in produce obtained from the control plant. In certain embodiments, such produce is a plant part. In certain embodiments of any of the aforementioned methods, the plant part is a seed, leaf, tuber, or root. In certain embodiments of any of the aforementioned methods, the applied composition coats or partially coats the plant part. In certain embodiments of the aforementioned methods, the composition is applied to the seed. In certain embodiments of any of the aforementioned methods, the *Meloidogyne* sp. is selected from the group consisting of *Meloidogyne arenaria*, *Meloidogyne exigua*, *Meloidogyne hapla*, *Meloidogyne graminis*, *Meloidogyne graminicola*, *Meloidogyne incognita*, and *Meloidogyne javanica*. In certain embodiments of any of the aforementioned methods, the plant part is selected from the group consisting of a *Brassica* sp. corn, wheat, rye, rice, alfalfa, rye, sorghum, millet, soybean, tobacco, potato, peanut, carrot, cotton, coffee, coconut, pineapple, sugar beet, strawberry, oat, barley, tomato, lettuce, pepper, pea, onion, green bean, and cucurbit plant part. In certain embodiments of any of the aforementioned methods, the composition further comprises a nematicide that provides for inhibition of RKN growth and/or reproduction and/or reductions in RKN-mediated plant damage. In certain embodiments where the composition further comprises a nematicide, the nematicide is selected from the group consisting of an organophosphate, biological, and a carbamate nematicide. In certain embodiments of any of the aforementioned methods, soil in which the plant is to be grown is surveyed for the presence of *Meloidogyne* sp. and the composition is applied to the plant part when the *Meloidogyne* sp. are present in the soil at a level that can result in reductions in plant growth, yield, water-deficit tolerance, chlorosis, produce quality, and combinations thereof to an untreated control plant. In certain embodiments of the methods, the composition is not applied to the plant part when the *Meloidogyne* sp. are present in the soil below levels that result in reductions in plant growth, yield, water-deficit tolerance, chlorosis, produce quality, and combinations thereof to an untreated control plant.

Plant parts that are at least partially coated with a composition comprising a *Methylobacterium* selected from the group consisting of *Methylobacterium* NLS0037 (NRRL B-50941), a derivative thereof, and a NLS0037-related *Methylobacterium* and an agriculturally acceptable excipient and/or an agriculturally acceptable adjuvant, wherein said composition is provided on said plant part in an amount that reduces *Meloidogyne* sp. damage to a plant grown from the plant part in comparison to a control plant grown from a control plant part that is not treated with the *Methylobacterium* are also provided. In certain embodiments, the amount of *Methylobacterium* present on said plant part is at least about $1\times10^3$ colony forming units (CFU) of said *Methylobacterium* per plant part. In certain embodiments, about $1\times10^2$, $1\times10^3$, or $1\times10^4$ CFU to about $1\times10^8$ or $1\times10^9$ CFU of the RKN-active *Methylobacterium* sp. are provided on a 100 mm² surface of the plant part. In certain embodiments, about $1\times10^2$, $1\times10^3$, or $1\times10^4$ CFU to about $1\times10^8$ or $1\times10^9$ CFU of the RKN-active *Methylobacterium* sp. are provided on the surface of a plant part that is a seed. In certain embodiments, the plant part is a seed, leaf, stem, root, or tuber. In certain embodiments, the NLS0037 derivative is obtained by mutagenizing or transforming *Methylobacterium* NLS0037. In certain embodiments, the NLS0037-related *Methylobacterium* is characterized by having a gene encoding a 16S RNA that has at least 95%, 97%, 98%, 99%, 99.5%, 99.7%, 99.9%, or 100% sequence identity across the entire length of SEQ ID NO:1. In certain embodiments of any of the aforementioned plant parts, the *Methylobacterium* is heterologous to the seed, tuber, or seedling. In certain embodiments of any of the aforementioned plant parts, the *Methylobacterium* is *Methylobacterium* NLS0037 (NRRL B-50941) and the plant part is not a tomato plant part. In certain embodiments of any of the aforementioned plant parts, the *Meloidogyne* sp. damage is selected from the group consisting of a reduction in plant growth, yield, water-deficit tolerance, chlorosis, produce quality, and combinations thereof. In certain embodiments of the aforementioned plant parts, the reduction in produce quality is evidenced by a decrease in the number of galls in produce obtained from the plant in comparison to the number of galls in produce obtained from the control plant. In certain embodiments, such produce is a plant part. In certain embodiments of any of the aforementioned plant parts, the *Meloidogyne* sp. is selected from the group consisting of *Meloidogyne arenaria*, *Meloidogyne exigua*, *Meloidogyne hapla*, *Meloidogyne graminis*, *Meloidogyne graminicola*, *Meloidogyne incognita*, and *Meloidogyne javanica*. In certain embodiments of any of the aforementioned plant parts, the plant part is selected from the group consisting of a *Brassica* sp. corn, wheat, rye, rice, alfalfa, rice, rye, sorghum, millet, soybean, tobacco, potato, peanut, carrot, cotton, coffee, coconut, pineapple, sugar beet, strawberry, oat, barley, tomato, lettuce, pepper, pea, onion, green bean, and cucurbit plant part.

Also provided are methods for controlling Root Knot Nematodes (RKN) damage to a plant that comprise: (i) applying a composition comprising an RKN-active *Methylobacterium* sp. to soil where a plant is growing or will be grown. In certain embodiments, the composition comprises a solid substance with adherent RKN-active *Methylobacterium* grown thereon or an emulsion having RKN-active *Methylobacterium* grown therein; and, (ii) growing a plant or a plant from seed in soil subjected to the application of the composition and in the presence of RKN. In certain embodiments of the methods, RKN damage sustained by the plant grown in the presence of the RKN is reduced in comparison to a control plant grown in the presence of the RKN. In certain embodiments of the methods, the composition comprises the RKN-active *Methylobacterium* sp. at a titer of about $5\times10^8$, $1\times10^9$, or $1\times10^{10}$ colony-forming units per gram of the solid substance to about $5\times10^{13}$ colony-forming units of *Methylobacterium* per gram of the solid substance or at a titer of about $1\times10^6$ CFU/mL to about $1\times10^9$ CFU/mL for the emulsion. In certain embodiments of the methods, the composition that is applied comprises the RKN-active *Methylobacterium* sp. at a titer of about $1\times10^4$ or $1\times10^5$ colony-forming units per ml to about $1\times10^9$, $1\times10^{10}$, $1\times10^{11}$, $5\times10^{11}$, or $1\times10^{12}$ colony-forming units of *Methylobacterium* per mL of a liquid or emulsion. In certain embodiments, about $1\times10^2$, $1\times10^3$, or $1\times10^4$ CFU to about $1\times10^8$ or $1\times10^9$ CFU of the RKN-active *Methylobacterium* sp. are provided on a 100 mm² surface of a plant part. In certain embodiments, about $1\times10^2$, $1\times10^3$, or $1\times10^4$ CFU to about $1\times10^8$ or $1\times10^9$ CFU of the RKN-active *Methylobacterium* sp. are provided on the surface of a seed. In certain embodiments of the methods, the RKN-active *Methylobacterium* sp. is a *Methylobacterium* isolate selected from the group consisting of *Methylobacterium* NLS0037, a derivative thereof, and a NLS0037-related *Methylobacterium*. In certain embodiments of any of the aforementioned methods, the composition is applied to the soil by broadcasting the composition, by drenching the soil with the composition, and/or by depositing the composition in furrow. In certain embodiments of the methods, the depositing in furrow is performed prior to placing seed in the furrow, at the same time as placing seed in the furrow, or after placing seed in the furrow. In certain embodiments of any of the aforementioned methods, the composition further comprises a nematicide that provides for inhibition of RKN growth and/or reproduction and/or reductions in RKN-mediated plant damage. In certain embodiments where the composition further comprises a nematicide, the nematicide is selected from the group consisting of an organophosphate, biological, and a carbamate nematicide. In certain embodiments of any of the aforementioned methods, soil in which the plant is to be grown is surveyed for the presence of *Meloidogyne* sp. and the composition is applied to the soil when the *Meloidogyne* sp. are present in the soil at a level that can result in reductions in plant growth, yield, water-deficit tolerance, chlorosis, produce quality, and combinations thereof to an untreated control plant. In certain embodiments of the methods, the composition is not applied to the soil when the *Meloidogyne* sp. are present in the soil below levels that result in reductions in plant growth, yield, water-deficit tolerance, chlorosis, produce quality, and combinations thereof to an untreated control plant.

Methods for treating a plant seed that can provide a Root Knot Nematodes (RKN) tolerant plant that comprises applying a composition comprising a RKN-active *Methylobacterium* sp. to a seed, thereby obtaining a treated seed that can provide a RKN tolerant plant are also provided. In certain embodiments of the methods, RKN damage sustained by the RKN tolerant plant grown from the treated seed and in the presence of the RKN is reduced in comparison to RKN damage sustained by a control plant grown from an untreated seed in the presence of RKN. In certain embodiments of the methods, the composition comprises a solid substance with adherent RKN-active *Methylobacterium* grown thereon or an emulsion having RKN-active *Methylobacterium* grown therein. In certain embodiments of the methods, the composition comprises the RKN-active *Methylobacterium* sp. at a titer of about $5\times10^8$, $1\times10^9$, or $1\times10^{10}$ colony-forming units per gram of the solid substance to about $5\times10^{13}$ colony-forming units of *Methylobacterium* per gram of the solid substance or at a titer of about $1\times10^6$ CFU/mL to about $1\times10^9$ CFU/mL for the emulsion. In certain embodiments of the methods, the composition comprises the RKN-active *Methylobacterium* sp. at a titer of about $1\times10^4$ or $1\times10^5$ colony-forming units per ml to about $1\times10^9$, $1\times10^{10}$, $6\times10^{10}$, $1\times10^{11}$, $5\times10^{11}$, or $1\times10^{12}$ colony-forming units of *Methylobacterium* per mL of a liquid or emulsion. In certain embodiments, about $1\times10^2$, $1\times10^3$, or $1\times10^4$ CFU to about $1\times10^8$ or $1\times10^9$ CFU of the RKN-active *Methylobacterium* sp. are provided on the surface of the seed. In certain embodiments of the methods, the RKN-active *Methylobacterium* sp. is a *Methylobacterium* isolate selected from the group consisting of *Methylobacterium* NLS0037, a derivative thereof, and a NLS0037-related *Methylobacterium*. In certain embodiments of any of the aforementioned methods, the applied composition coats or partially coats the seed. Also provided herein are treated seeds obtained by any of the aforementioned methods. In certain embodiments of any of the aforementioned methods, the composition further comprises a nematicide that provides for inhibition of RKN growth and/or reproduction and/or reductions in RKN-mediated plant damage. In certain embodiments where the composition further comprises a nematicide, the nematicide is selected from the group consisting of an organophosphate, biological, and a carbamate nematicide.

Also provided herein are methods for controlling Root Knot Nematodes (RKN) damage to a plant that comprise: (i) planting a seed that has been treated with a composition comprising a RKN-active *Methylobacterium* sp.; and, (ii) growing a RKN-tolerant plant from the treated seed in the presence of RKN. In certain embodiments of the methods, the RKN damage sustained by the RKN-tolerant plant grown in the presence of the RKN is reduced in comparison to RKN damage sustained by a control plant grown from untreated seed in the presence of RKN. In certain embodiments of the methods, the seed was treated with a composition that comprises a solid substance with adherent RKN-active *Methylobacterium* grown thereon or an emulsion having RKN-active *Methylobacterium* grown therein. In certain embodiments of the methods, the composition comprises the RKN-active *Methylobacterium* sp. at a titer of about $5\times10^8$, $1\times10^9$, or $1\times10^{10}$ colony-forming units per gram of the solid substance to about $5\times10^{13}$ colony-forming units of *Methylobacterium* per gram of the solid substance or at a titer of about $1\times10^6$ CFU/mL to about $1\times10^9$ CFU/mL for the emulsion. In certain embodiments of the methods, the composition comprises the RKN-active *Methylobacterium* sp. at a titer of about $1\times10^4$ or $1\times10^5$ colony-forming units per ml to about $1\times10^9$, $1\times10^{10}$, $1\times10^{11}$, $5\times10^{11}$, or $1\times10^{12}$ colony-forming units of *Methylobacterium* per mL of a liquid or emulsion. In certain embodiments, about $1\times10^2$, $1\times10^3$, or $1\times10^4$ CFU to about $1\times10^8$ or $1\times10^9$ CFU of the RKN-active *Methylobacterium* sp. are provided on the surface of the seed. In certain embodiments of the methods, the RKN-active *Methylobacterium* sp. is a *Methylobacterium* isolate selected from the group consisting of *Methylobacterium* NLS0037, a derivative thereof, and a NLS0037-related *Methylobacterium*. In certain embodiments of any of the aforementioned methods, the applied composition coats or partially coats the seed. In certain embodiments of any of the aforementioned methods, the composition further comprises a nematicide that provides for inhibition of RKN growth and/or reproduction and/or reductions in RKN-mediated plant damage. In certain embodiments where the composition further comprises a nematicide, the nematicide is selected from the group consisting of a organophosphate, biological, and a carbamate nematicide.

Also provided are compositions comprising a RKN-active *Methylobacterium* sp. and an agriculturally acceptable adjuvant and/or and agriculturally acceptable excipient. In certain embodiments, the composition comprises a solid substance with adherent RKN-active *Methylobacterium* grown thereon or an emulsion having RKN-active *Methylobacterium* grown therein. In certain embodiments, the composition comprises the RKN-active *Methylobacterium* sp. at a titer of about $5\times10^8$, $1\times10^9$, or $1\times10^{10}$ colony-forming units per gram of the solid substance to about $5\times10^{13}$ colony-forming units of *Methylobacterium* per gram of the solid substance or at a titer of about $1\times10^6$ CFU/mL to about $1\times10^9$ CFU/mL for the emulsion. In certain embodiments, the composition comprises the RKN-active *Methylobacterium* sp. at a titer of about $1\times10^4$ or $1\times10^5$ colony-forming units per ml to about $1\times10^9$, $1\times10^{10}$, or $6\times10^{10}$ colony-forming units of *Methylobacterium* per mL of a liquid or emulsion. In certain embodiments, about $1\times10^2$, $1\times10^3$, or $1\times10^4$ CFU to about $1\times10^8$ or $1\times10^9$ CFU of the RKN-active *Methylobacterium* sp. are provided on a 100 mm$^2$ surface of a plant part. In certain embodiments, about $1\times10^2$, $1\times10^3$, or $1\times10^4$ CFU to about $1\times10^8$ or $1\times10^9$ CFU of the RKN-active *Methylobacterium* sp. are provided on the surface of a seed. In certain embodiments, the RKN-active *Methylobacterium* sp. is selected from the group consisting of *Methylobacte-*

*rium* NLS0037, a derivative thereof, and a NLS0037-related *Methylobacterium*. In certain embodiments, the composition further comprises a nematicide that provides for inhibition of RKN growth and/or reproduction and/or reductions in RKN-mediated plant damage. In certain embodiments, the nematicide is selected from the group consisting of a organophosphate, biological, and a carbamate nematicide. In any of the aforementioned compositions, the composition can be in a liquid form or in a dry form. In certain embodiments, the composition is in a dry, lyophilized form and further comprises a cryoprotectant. In certain embodiments, the compositions will be essentially free of contaminating microorganisms or free of contaminating microorganisms.

In certain embodiments of any of the aforementioned compositions comprising RKN-active *Methylobacterium* sp., plants or plant part that is coated or partially coated with a composition comprising a RKN-active *Methylobacterium* sp., methods of using the compositions to control RKN damage to plants, plant parts, and plants derived therefrom, and methods of making the compositions, the *Methylobacterium* sp. is heterologous to the plant or plant part to which it is applied.

In certain embodiments of any of the aforementioned compositions comprising RKN-active *Methylobacterium* sp., plants or plant part that is coated or partially coated with a composition comprising a RKN-active *Methylobacterium* sp., methods of using the compositions to control RKN damage to plants, plant parts, and plants derived therefrom, and methods of making the compositions, the RKN-active *Methylobacterium* sp. is a derivative of a *Methylobacterium* sp. NLS0037.

In certain embodiments of any of the aforementioned compositions, methods, plant, or plant parts, the RKN-active *Methylobacterium* sp. has a 16S RNA encoding sequence that has significant sequence identity to the 16S RNA encoding sequence of a RKN-active *Methylobacterium* sp. provided herein. In certain embodiments, the RKN-active *Methylobacterium* sp. has a 16S RNA encoding sequence that has at least 95%, 96%, 97%, 98%, 99%, or 99.5% sequence identity across the entire length of the 16S RNA encoding sequence of the RKN-active *Methylobacterium* sp. isolate NLS0037 provided herein. A RKN active *Methylobacterium* sp. that can be used in any of the composition, plants or plant parts that are coated or partially coated with the compositions, methods of using the compositions to control RKN damage to plants, plant parts, and plants derived therefrom, and methods of making the compositions can be RKN active *Methylobacterium* sp. can be at least 95%, 96%, 97%, 98%, 99%, or 99.5% sequence identity across the entire length of the 16S RNA encoding sequences of SEQ ID NO: 1.

BRIEF DESCRIPTION OF THE DRAWINGS

Not Applicable.

DESCRIPTION

Definitions

As used herein, the phrases "adhered thereto" and "adherent" refer to *Methylobacterium* that are associated with a solid substance by growing, or having been grown, on a solid substance.

As used herein, the phrase "agriculturally acceptable adjuvant" refers to a substance that enhances the performance of an active agent in a composition for treatment of plants and/or plant parts. In certain compositions, an active agent can comprise a mono-culture or co-culture of *Methylobacterium*.

As used herein, the phrase "agriculturally acceptable excipient" refers to an essentially inert substance that can be used as a diluent and/or carrier for an active agent in a composition for treatment of plants and/or plant parts. In certain compositions, an active agent can comprise a mono-culture or co-culture of *Methylobacterium*.

As used herein, the term "*Methylobacterium*" refers to bacteria that are facultative methylotrophs of the genus *Methylobacterium*. The term *Methylobacterium*, as used herein, thus does not encompass species in the genera *Methylobacter*, *Methylomonas*, *Methylomicrobium*, *Methylococcus*, *Methylosinus*, *Methylocystis*, *Methylosphaera*, *Methylocaldum*, and *Methylocella*, which are obligate methanotrophs.

As used herein, the phrase "control plant" refers to a plant that had not received treatment with a RKN-active *Methylobacterium* or composition comprising the same at either the seed or any subsequent stage of the control plant's development. Control plants include, but are not limited to, non-transgenic plants, transgenic plants having a transgene-conferred RKN resistance trait, and plants treated with, or grown in soil treated with, an insecticidal compound or other agent that can protect a plant from RKN feeding.

As used herein, the terms "Root Knot Nematodes" and "RKN" are used interchangeable to refer to the juvenile or adult forms of any nematode of the genus *Meloidogyne*.

As used herein, the phrase "co-culture of *Methylobacterium*" refers to a *Methylobacterium* culture comprising at least two strains of *Methylobacterium* or at least two species of *Methylobacterium*.

As used herein, the phrase "contaminating microorganism" refers to microorganisms in a culture, fermentation broth, fermentation broth product, or composition that were not identified prior to introduction into the culture, fermentation broth, fermentation broth product, or composition.

As used herein, the phrase "derivatives thereof", when used in the context of a *Methylobacterium* isolate, refers to any strain that is obtained from the *Methylobacterium* isolate. Derivatives of a *Methylobacterium* isolate include, but are not limited to, variants of the strain obtained by selection, variants of the strain selected by mutagenesis and selection, and genetically transformed strains obtained from the *Methylobacterium* isolate.

As used herein, the term "emulsion" refers to a colloidal mixture of two immiscible liquids wherein one liquid is the continuous phase and the other liquid is the dispersed phase. In certain embodiments, the continuous phase is an aqueous liquid and the dispersed phase is liquid that is not miscible, or partially miscible, in the aqueous liquid.

As used herein, the phrase "essentially free of contaminating microorganisms" refers to a culture, fermentation broth, fermentation product, or composition where at least about 95% of the microorganisms present by amount or type in the culture, fermentation broth, fermentation product, or composition are the desired *Methylobacterium* or other desired microorganisms of pre-determined identity.

As used herein, the term "heterologous", when used in the context of *Methylobacterium* that at least partially coats a plant or plant part, refers to a *Methylobacterium* that is not naturally associated with a plant or plant part of the same species as the plant or plant part that is at least partially coated with the *Methylobacterium*. In certain embodiments, the heterologous *Methylobacterium* that is used to at least partially coat a plant or plant part of a first plant species is a *Methylobacterium* that was isolated, or can be isolated, from a second and distinct plant species.

As used herein, the phrase "inanimate solid substance" refers to a substance which is insoluble or partially soluble in water or aqueous solutions and which is either non-living or which is not a part of a still-living organism from which it was derived.

As used herein, the phrase "mono-culture of *Methylobacterium*" refers to a *Methylobacterium* culture consisting of a single strain of *Methylobacterium*.

As used herein, the phrase "partially coated", when used in the context of a composition comprising a RKN-active *Methylobacterium* sp. and a plant part (e.g., a seed), refers to a plant part where at least 10%, 20%, 40%, 50%, 60%, 70%, 80%, 90%, or 95% of the surface area of the plant part is coated with the composition.

As used herein, the term "peptide" refers to any polypeptide of 50 amino acid residues or less.

As used herein, the term "protein" refers to any polypeptide having 51 or more amino acid residues.

As used herein, a "pesticide" refers to an agent that is insecticidal, fungicidal, nematocidal, bacteriocidal, or any combination thereof.

As used herein, the phrase "bacteriostatic agent" refers to agents that inhibit growth of bacteria but do not kill the bacteria.

As used herein, the phrase "pesticide does not substantially inhibit growth of said *Methylobacterium*" refers to any pesticide that when provided in a composition comprising a fermentation product comprising a solid substance wherein a mono-culture or co-culture of *Methylobacterium* is adhered thereto, results in no more than a 50% inhibition of *Methylobacterium* growth when the composition is applied to a plant or plant part in comparison to a composition lacking the pesticide. In certain embodiments, the pesticide results in no more than a 40%, 20%, 10%, 5%, or 1% inhibition of *Methylobacterium* growth when the composition is applied to a plant or plant part in comparison to a composition lacking the pesticide.

As used herein, the term "PPFM bacteria" refers without limitation to bacterial species in the genus *Methylobacterium* other than *M. nodulans*.

As used herein, the phrase "solid substance" refers to a substance which is insoluble or partially soluble in water or aqueous solutions.

As used herein, the phrase "solid phase that can be suspended therein" refers to a solid substance that can be distributed throughout a liquid by agitation.

As used herein, the term "non-regenerable" refers to either a plant part or processed plant product that cannot be regenerated into a whole plant.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

RKN-active *Methylobacterium*, Compositions Comprising RKN-active *Methylobacterium*, Methods of their Use, and Methods of Making Various RKN-active *Methylobacterium* isolates, compositions comprising these *Methylobacterium*, methods of using the compositions to inhibit RKN growth or reproduction and/or reduce RKN damage to a plant, and methods of making the compositions are provided herein. As used herein, inhibition of the growth of a RKN includes any measurable decrease in RKN growth and/or reproduction, where RKN growth and/or reproduction includes, but is not limited to, any measurable increase in the juvenile weight, and/or any progression through juvenile development of from juvenile to adult development. As used herein, inhibition of RKN growth and/or reproduction and/or reduction of RKN damage to a plant are also understood to include any measurable decrease in RKN infection and/or the adverse effects caused by RKN feeding on a plant. Adverse effects of RKN infection on a plant include, but are not limited to, deformation and/or reductions in root systems, reductions in top growth, any type of tissue damage or necrosis, increased incidence of fungal or bacterial disease, any type of yield reduction, and/or decreased water-deficit tolerance.

Isolated RKN-active *Methylobacterium* sp. are provided herein. In certain embodiments, the *Methylobacterium* is selected from the group consisting of *M. aminovorans, M. extorquens, M. fujisawaense, M. mesophilicum, M. radiotolerans, M. rhodesianum, M. nodulans, M. phyllosphaerae, M. thiocyanatum*, and *M. oryzae*. In certain embodiments, *Methylobacterium* is not *M. radiotolerans* or *M. oryzae*. In certain embodiments, the RKN-active *Methylobacterium* isolate is selected from the group consisting of *Methylobacterium* NLS0037, a derivative thereof, and a NLS0037-related *Methylobacterium*. In certain embodiments, the RKN-active *Methylobacterium* isolate is selected from the group consisting of *Methylobacterium* NLS0037 and a derivative thereof. In certain embodiments, the RKN-active *Methylobacterium* provides for at least about 25%, at least about 50%, or at least about 75% reductions in RKN damage to a treated plant, plant arising from a treated seed, or plant grown in soil treated with the RKN in comparison to untreated control plants, plants arising from untreated seeds, or plants grown in untreated soils upon exposure to a RKN. In certain embodiments, the RKN-active *Methylobacterium* provides for a decrease in a root-knot index score for galling or egg masses in the treated plant, plant part, or a plant derived therefrom relative to an untreated control plant, plant part, or a plant derived therefrom. In certain embodiments, the RKN that is inhibited is selected from the group consisting of a *Meloidogyne arenaria, Meloidogyne exigua, Meloidogyne hapla, Meloidogyne graminis, Meloidogyne graminicola, Meloidogyne incognita*, and *Meloidogyne javanica*. species.

In certain embodiments, the RKN-active *Methylobacterium* provides for at least about 25%, at least about 50%, or at least about 75% reductions in RKN growth and/or reproduction on a treated plant, plant arising from a treated seed, or plant grown in soil treated with the RKN-active *Methylobacterium* in comparison to a untreated control plants, plants arising from untreated seeds, or plants grown in untreated soils upon exposure to a RKN. In certain embodiments, the RKN-active *Methylobacterium* is a *Methylobacterium* that inhibits a *Meloidogyne* sp. is selected from the group consisting of a *Meloidogyne arenaria, Meloidogyne exigua, Meloidogyne hapla, Meloidogyne graminis, Meloidogyne graminicola, Meloidogyne incognita*, and *Meloidogyne javanica* species. In certain embodiments of any of the aforementioned compositions, the composition comprises a solid substance wherein a mono-culture or co-culture of *Methylobacterium* is adhered thereto. In certain embodiments where the *Methylobacterium* is adhered to a solid substance, the composition comprises a colloid formed by the solid substance wherein a mono-culture or co-culture of *Methylobacterium* is adhered thereto and a liquid. In certain embodiments, the colloid is a gel. In certain embodiments of certain aforementioned compositions, composition is an emulsion that does not contain a solid substance. In certain embodiments of any of the aforementioned compositions, the RKN-active *Methylobacterium* is selected from the group consisting of *Methylobacterium* NLS0037, a derivative thereof, and a NLS0037-related *Methylobacterium*. In certain embodiments of any of the aforementioned compositions, the RKN-active *Methylobacterium* is selected from the group consisting of *Methylobacterium* NLS0037 and a derivative thereof.

In certain embodiments, isolated RKN-active *Methylobacterium* sp. can be identified by treating a plant, a seed, soil in which the plant or a plant arising from the seed are grown, or other plant growth media in which the plant or a plant arising from the seed are grown and assaying for either reductions in RKN damage, RKN growth, RKN reproduction, RKN feeding activity, and combinations thereof. In still other embodiments, the RKN-active *Methylobacterium* sp., compositions comprising the same, fermentation products comprising the same, cell free exudates therefrom, or compounds derived therefrom can be exposed to juvenile RKN and assayed for inhibition of juvenile growth, development, behavior, or feeding activity. Various assays that can adapted for use in identifying RKN-active *Methylobacterium* sp. are disclosed in U.S Patent Application Publication US20130142759, which is incorporated herein by reference in its entirety.

In certain embodiments, the RKN-active *Methylobacterium* sp. has a 16S RNA encoding sequence that has significant sequence identity to the 16S RNA encoding sequence of a RKN-active *Methylobacterium* sp. provided herein. In certain embodiments, the RKN-active *Methylobacterium* sp. has a 16S RNA encoding sequence that has at least 95%, 96%, 97%, 98%, 99%, or 99.5% sequence identity across the entire length of the 16S RNA encoding sequence of the RKN-active *Methylobacterium* sp. isolate NLS0037. A RKN active *Methylobacterium* sp. that can be used in any of the composition, plants or plant parts that are coated or partially coated with the compositions, methods of using the compositions to control RKN damage to plants, plant parts, and plants derived therefrom, and methods of making the compositions can be RKN active *Methylobacterium* sp. can be at least 95%, 96%, 97%, 98%, 99%, or 99.5% sequence identity across the entire length of the 16S RNA encoding sequences of SEQ ID NO:1. The 16S RNA encoding sequence of SEQ ID NO:1 is set forth in Table 1.

TABLE 1

16S RNA encoding sequences

| Isolate (NLS No.) | SEQ ID NO: | DNA sequence encoding the 16S RNA |
|---|---|---|
| NLS0037 | SEQ ID NO: 1 | GGTGATCCAGCCGCAGGTTCCCCTACGGC TACCTTGTTACGACTTCACCCCAGTCGCTG ACCCTACCGTGGTCGCCTGCCTCCTTGCGG TTGGCGCAGCGCCGTCGGGTAAGACCAAC TCCCATGGTGTGACGGGCGGTGTGTACAA GGCCCGGGAACGTATTCACCGTGGCATGC TGATCCACGATTACTAGCGATTCCGCCTTC ATGCACCCGAGTTGCAGAGTGCAATCCGA ACTGAGACGGCTTTTGGGGATTTGCTCCAG GTCGCCCCTTCGCGTCCCACTGTCACCGCC ATTGTAGCACGTGTGTAGCCCATCCCGTAA GGGCCATGAGGACTTGACGTCATCCACAC CTTCCTCGCGGCTTATCACCGGCAGTCTCC CTAGAGTGCCCAACTGAATGATGGCAACT AAGGACGTGGGTTGCGCTCGTTGCGGGAC TTAACCCAACATCTCACGACACGAGCTGA CGACAGCCATGCAGCACCTGTGTGCGCGC CTCCGAAGAGGACTGGGAATCTCTCCCCA TAACACGCCATGTCAAAGGATGGTAAGGT TCTGCGCGTTGCTTCGAATTAAACCACATG CTCCACCGCTTGTGCGGGCCCCCGTCAATT CCTTTGAGTTTTAATCTTGCGACCGTACTC CCCAGGCGGAATGCTCAAAGCGTTAGCTG CGCTACTGAGGTGCAAGCACCCCAACAGC TGGCATTCATCGTTTACGGCGTGGACTACC AGGGTATCTAATCCTGTTTGCTCCCCACGC TTTCGCGCCTCAGCGTCAGTAATGGTCCAG TTGGCCGCCTTCGCCACCGGTGTTCTTGCG AATATCTACGAATTTCACCTCTACACTCGC AGTTCCACCAACCTCTACCATACTCAAGCG TCCCAGTATCGAAGGCCATTCTGTGGTTGA GCCACAGGCTTTCACCCCCGACTTAAAAC GCCGCCTACGCGCCCTTTACGCCCAGTGAT TCCGAGCAACGCTAGCCCCCTTCGTATTAC CGCGGCTGCTGGCACGAAGTTAGCCGGGG CTTATTCCTCCGGTACCGTCATTATCGTCC CGGATAAAAGAGCTTTACAACCCTAAGGC CTTCATCACTCACGCGGCATGGCTGGATCA GGCTTGCGCCCATTGTCCAATATTCCCCAC TGCTGCCTCCCGTAGGAGTCTGGGCCGTGT CTCAGTCCCAGTGTGGCTGATCATCCTCTC AGACCAGCTACTGATCGTCGCCTTGGTGA GCCGTTACCTCACCAACTAGCTAATCAGA CGCGGGCCGATCCTCCGGCAGCAAGCCTT TCCCCAAAAGGGCGTATCCGGTATTAGCT CAAGTTTCCCTGAGTTATTCCGAACCAGAG GGCACGTTCCCACGCGTTACTCACCCGTCC |

TABLE 1-continued

16S RNA encoding sequences

| Isolate (NLS No.) | SEQ ID NO: | DNA sequence encoding the 16S RNA |
|---|---|---|
| | | GCCGCTGACACCCGAAAGTGCCCGCTCGA CTTGCATGTGTTAAGCCTGCCGCCAGCGTT CGCTCTGAGCCAGGATCAAACTCTC |

Various *Methylobacterium* sp. isolates provided herein are disclosed in Table 2.

TABLE 2

*Methylobacterium* sp. Isolates

| NLS No. | USDA ARS NRRL No.[1] |
|---|---|
| NLS0037 | NRRL B-50941 |

[1]Deposit number for strain deposited with the AGRICULTURAL RESEARCH SERVICE CULTURE COLLECTION (NRRL) of the National Center for Agricultural Utilization Research, Agricultural Research Service, U.S. Department of Agriculture, 1815 North University Street, Peoria, Illinois 61604 U.S.A. under the terms of the Budapest Treaty on the International Recognition of the Deposit of Microorganisms for the Purposes of Patent Procedure. Subject to 37 CFR §1.808(b), all restrictions imposed by the depositor on the availability to the public of the deposited material will be irrevocably removed upon the granting of any patent from this patent application.

Also provided herein are methods for controlling RKN that comprise applying any of the aforementioned compositions provided herein to a plant or a plant part in an amount that provides for inhibition of RKN damage in the plant, plant part, or a plant obtained therefrom relative to infection of a control plant, plant part, or plant obtained therefrom that had not received an application of the composition. In certain embodiments, application of the composition provides for at least about 5%, at least about 10%, at least about 20%, at least about 30%, at least about 40%, at least about 50%, at least about 75%, at least about 85%, or at least about 95% reduction of RKN damage in the plant, plant part, or a plant derived therefrom relative to RKN damage of the control plant, plant part, or plant obtained therefrom. In certain embodiments, application of the composition provides for at least about 5%, at least about 10%, at least about 20%, at least about 30%, at least about 40%, at least about 50%, at least about 75%, at least about 85%, or at least about 95% reduction of RKN reproduction in the plant, plant part, or a plant derived therefrom relative to RKN reproduction in the control plant, plant part, or plant obtained therefrom. In certain embodiments, the methods provide for a decrease in a root-knot index score for galling or egg masses in the treated plant, plant part, or a plant derived therefrom relative to an untreated control plant, plant part, or a plant derived therefrom. In certain embodiments, the plant part is selected from the group consisting of a leaf, a stem, a flower, a root, a tuber, a pollen grain, and a seed. In certain embodiments, the method further comprises the step of harvesting at least one plant part selected from the group consisting of a leaf, a stem, a flower, a root, a tuber, a pollen grain, or a seed from the plant or plant part. In certain embodiments of any of the aforementioned methods, the methods further comprise obtaining a processed food or feed composition from the plant or plant part. In certain embodiments, the processed food or feed composition is a meal or a paste. In certain embodiments of any of the aforementioned methods, the RKN-active *Methylobacterium* is selected from the group consisting of *Methylobacterium* NLS0037, a derivative thereof, and a NLS0037-related *Methylobacterium*. In certain embodiments, the RKN-active *Methylobacterium* is selected from the group consisting of *Methylobacterium* NLS0037 and a derivative thereof.

Also provided are methods of making the compositions useful for controlling RKN that comprise combining a RKN-active *Methylobacterium* with an agriculturally acceptable excipient and/or with an agriculturally acceptable adjuvant. In certain embodiments of the methods, the *Methylobacterium* sp., is selected from the group consisting of *M. aminovorans, M. extorquens, M. fujisawaense, M. mesophilicum, M. radiotolerans, M. rhodesianum, M. nodulans, M. phyllosphaerae, M. thiocyanatum*, and *M. oryzae*. In certain embodiments of the methods, the *Methylobacterium* is adhered to a solid substance. In certain embodiments of the methods, the *Methylobacterium* is adhered to the solid substance is combined with a liquid to form a composition that is a colloid. In certain embodiments of the methods, the colloid is a gel. In certain embodiments of the methods, the *Methylobacterium* adhered to the solid substance is provided by culturing the *Methylobacterium* in the presence of the solid substance. In certain embodiments of the methods, the composition comprises an emulsion. In certain embodiments of the methods, the *Methylobacterium* is provided by culturing the *Methylobacterium* in an emulsion. In certain embodiments of any of the aforementioned methods, the RKN-active *Methylobacterium* is selected from the group consisting of *Methylobacterium* NLS0037, a derivative thereof, and a NLS0037-related *Methylobacterium*. In certain embodiments, the RKN-active *Methylobacterium* is selected from the group consisting of *Methylobacterium* NLS0037 and a derivative thereof.

Methods where *Methylobacterium* are cultured in biphasic media comprising a liquid phase and a solid substance have been found to significantly increase the resultant yield of *Methylobacterium* relative to methods where the *Methylobacterium* are cultured in liquid media alone. In certain embodiments, the methods can comprise growing the *Methylobacterium* in liquid media with a particulate solid substance that can be suspended in the liquid by agitation under conditions that provide for *Methylobacterium* growth. In certain embodiments where particulate solid substances are used, at least substantially all of the solid phase can thus be suspended in the liquid phase upon agitation. Such particulate solid substances can comprise materials that are about 1 millimeter or less in length or diameter. In certain embodiments, the degree of agitation is sufficient to provide for uniform distribution of the particulate solid substance in the liquid phase and/or optimal levels of culture aeration. However, in other embodiments provided herein, at least substantially all of the solid phase is not suspended in the liquid phase, or portions of the solid phase are suspended in the liquid phase and portions of the solid phase are not suspended in the liquid phase. Non-particulate solid substances can be used in certain biphasic media where the solid phase is not suspended in the liquid phase. Such non-particulate solid substances include, but are not limited to, materials that are greater than about 1 millimeter in length or diameter. Such particulate and non-particulate solid substances also include, but are not limited to, materials that are porous, fibrous, or otherwise configured to provide for increased surface areas for adherent growth of the *Methylobacterium*. Biphasic media where portions of the solid phase are suspended in the liquid phase and portions of the solid phase are not suspended in the liquid phase can comprise a mixture of particulate and non-particulate solid substances. Such particulate and non-particulate solid substances used in any of the aforementioned biphasic media also include, but are not limited to, materials that are porous, fibrous, or otherwise configured to provide for increased surface areas for adherent growth of the *Methylobacterium*. In certain embodiments, the media comprises a colloid formed by a solid and a liquid phase. A colloid comprising a solid and a liquid can be pre-formed and added to liquid media or can be formed in media containing a solid and a liquid. Colloids comprising a solid and a liquid can be formed by subjecting certain solid substances to a chemical and/or thermal change. In certain embodiments, the colloid is a gel. In certain embodiments, the liquid phase of the media is an emulsion. In certain embodiments, the emulsion comprises an aqueous liquid and a liquid that is not miscible, or only partially miscible, in the aqueous liquid. Liquids that are not miscible, or only partially miscible, in water include, but are not limited to, any of the following: (1) liquids having a miscibility in water that is equal to or less than that of pentanol, hexanol, or heptanol at 25 degrees C.; (2) liquids comprising an alcohol, an aldehyde, a ketone, a fatty acid, a phospholipid, or any combination thereof; (3) alcohols selected from the group consisting of aliphatic alcohols containing at least 5 carbons and sterols; (4) an animal oil, microbial oil, synthetic oil, plant oil, or combination thereof; and/or, (5) a plant oil is selected from the group consisting of, soybean, cotton, peanut, sunflower, olive, flax, coconut, palm, rapeseed, sesame seed, safflower, and combinations thereof. In certain embodiments, the immiscible or partially immiscible liquid can comprises at least about 0.02% to about 20% of the liquid phase by mass. In certain embodiments, the methods can comprise obtaining a biphasic culture media comprising the liquid, the solid, and *Methylobacterium* and incubating the culture under conditions that provide for growth of the *Methylobacterium*. Biphasic culture medias comprising the liquid, the solid, and *Methylobacterium* can be obtained by a variety of methods that include, but are not limited to, any of: (a) inoculating a biphasic media comprising the liquid and the solid substance with *Methylobacterium*; (b) inoculating the solid substance with *Methylobacterium* and then introducing the solid substance comprising the *Methylobacterium* into the liquid media; (c) inoculating the solid substance with *Methylobacterium*, incubating the *Methylobacterium* on the solid substance, and then introducing the solid substance comprising the *Methylobacterium* into the liquid media; or (d) any combination of (a), (b), or (c). Methods and compositions for growing *Methylobacterium* in biphasic media comprising a liquid and a solid are disclosed in co-assigned U.S. Pat. No. 9,181,541, issued Nov. 10, 2015, which is incorporated herein by reference in its entirety. Compositions comprising dried formulations of *Methylobacterium* that are adhered to solid substances, methods for making such compositions, and methods of applying those compositions to plants and plant parts including seeds are disclosed in co-assigned U.S. patent application Ser. No. 14/856,020, filed Sep. 16, 2015, published as US20160073641, and which is incorporated herein by reference in its entirety.

Methods where *Methylobacterium* are cultured in media comprising an emulsion have also been found to significantly increase the resultant yield of *Methylobacterium* relative to methods where the *Methylobacterium* are cultured in liquid media alone. In certain embodiments, the methods for making the compositions provided herein can comprise growing the RKN-active *Methylobacterium* agent in an emulsion under conditions that provide for *Methylobacterium* growth. Medias comprising the emulsion and RKN-active *Methylobacterium* can be obtained by a variety of methods that include, but are not limited to, any of: (a) inoculating a media comprising the emulsion with *Methylobacterium*; (b) inoculating the aqueous liquid with the *Methylobacterium*, introducing the non-aqueous liquid, and mixing to form an emulsion; (c) inoculating the aqueous liquid with the *Methylobacterium*, introducing the non-aqueous liquid, and mixing to form an emulsion; or (d) any combination of (a), (b), or (c). In certain embodiments, the emulsion comprises an aqueous liquid and a liquid that is not miscible, or only partially miscible, in the aqueous liquid. Non-aqueous liquids that are not miscible, or only partially miscible, in water include, but are not limited to, any of the following: (1) liquids having a miscibility in water that is equal to or less than that of n-pentanol, n-hexanol, or n-heptanol at 25 degrees C.; (2) liquids comprising an alcohol, an aldehyde, a ketone, a fatty acid, a phospholipid, or any combination thereof; (3) alcohols is selected from the group consisting of aliphatic alcohols containing at least 5, 6, or 7 carbons and sterols; (4) an animal oil, microbial oil, synthetic oil, plant oil, or combination thereof; and/or, (5) a plant oil is selected from the group consisting of, soybean, cotton, peanut, sunflower, olive, flax, coconut, palm, rapeseed, sesame seed, safflower, and combinations thereof. In certain embodiments, the immiscible or partially immiscible non-aqueous liquid can comprise at least about 0.02% to about 20% of the emulsion by mass. In certain embodiments, the immiscible or partially immiscible non-aqueous liquid can comprise at least about any of about 0.05%, 0.1%, 0.5%, or 1% to about 3%, 5%, 10%, or 20% of the emulsion by mass. Methods and compositions for growing *Methylobacterium* in media comprising an emulsion are disclosed in co-assigned International Patent Application PCT/US14/40218, filed May 30, 2014, and co-assigned US patent application publication US20160120188, which are incorporated herein by reference in their entireties.

In certain embodiments, the fermentation broth, fermentation broth product, or compositions that comprise RKN-active *Methylobacterium* sp. can further comprise one or more introduced microorganisms of pre-determined identity other than *Methylobacterium*. Other microorganisms that can be added include, but are not limited to, microorganisms that are biopesticidal or provide some other benefit when applied to a plant or plant part. Biopesticidal or otherwise beneficial microorganisms thus include, but are not limited to, various *Bacillus* sp., *Pseudomonas* sp., *Coniothyrium* sp., *Pantoea* sp., *Streptomyces* sp., and *Trichoderma* sp. Microbial biopesticides can be a bacterium, fungus, virus, or protozoan. Particularly useful biopesticidal microorganisms include various *Bacillus subtilis, Bacillus thuringiensis, Bacillus pumilis* (e.g., *Bacillus pumilis* strain QST2808), *Pseudomonas syringae, Trichoderma harzianum, Trichoderma virens,* and *Streptomyces lydicus* strains. Biopesticidal microorganisms that can be used include, but are not limited to, the *Bacillus pumilis* strains described in US Patent Application Publication No. US20130142759, and the *Bacillus cereus* and *Bacillus firmus* strains disclosed in U.S. Pat. No. 6,406,690, each of which are incorporated herein by reference in their entireties. Other microorganisms that are added can be genetically engineered or other isolates that are available as pure cultures. In certain embodiments, it is anticipated that the bacterial or fungal microorganism can be provided in the fermentation broth, fermentation broth product, or composition in the form of a spore.

In certain embodiments, the RKN-active *Methylobacterium* sp. and compositions comprising the same that are provided herein can be used in conjunction with transgenic plants that express gene products that are inhibitory to growth of certain RKN. Such transgenic plants include, but are not limited to, those expressing interfering RNA molecules that suppress endogenous RKN genes (U.S. Patent Appl. Publication No. US20120030834; PCT Appl. No. WO2014091466) or Root-Knot Nematode Resistance genes (U.S. Patent Appl. Publication No. US20110162102). Each of the aforementioned patent applications cited in reference to such transgenic plants is incorporated herein by reference in their entireties.

In certain embodiments, the RKN-active *Methylobacterium* sp. and compositions comprising the same that are provided herein can be used in conjunction with plants that comprise one or more genetic loci that can confer resistance to RKN. Such RKN resistant plants include, but are not limited to, tomato plants comprising the Mi gene (Milligan et al. The Plant Cell Aug. 1998 vol. 10 no. 8 1307-1319) or pepper plants comprising the Me, N, or Tabasco genes (Brito et al. J Nematol. 2007 Dec.; 39(4): 327-332).

In certain embodiments, the RKN-active *Methylobacterium* sp. and compositions comprising the same that are provided herein can be used in conjunction with, or comprise, nematicides that also provide for inhibition of RKN growth and/or reproduction and/or reductions in RKN-mediated plant damage. Such nematicides can be used in soil treatments (drenches, in furrow deposits, and the like) and/or in seed treatments. In certain embodiments, the nematicide is selected from the group consisting of organophosphate, biological, and carbamate nematicides. In certain embodiments, the seed is treated with one or more of the aforementioned nematicides (U.S. Pat. Nos. 6,660,690 and 8,080, 496, each incorporated herein by reference in their entireties). Commercial soil applied nematicide formulations that can be used in conjunction with the RKN-active *Methylobacterium* sp. provided herein include, but are not limited to, formulations containing the carbamates aldicarb, aldoxycarb, oxamyl, carbofuran, and cleothocarb, and/or the organophosphates thionazin, ethoprophos, fenamiphos, fensulfothion, and/or terbufos formulations. Combinations of the aforementioned nematicides and the aforementioned transgenic plants that provide for inhibition of RKN growth and/or reproduction and/or reductions in RKN-mediated plant damage can also be used in conjunction with the RKN-active *Methylobacterium* sp. provided herein.

In certain embodiments, any of the aforementioned compositions comprising RKN-active *Methylobacterium* sp. provided herein are selectively applied to plant parts or to soil or other media in which a plant is or is to be grown, or plant parts subjected to such applications are used in soil or media, following a determination that *Meloidogyne* levels in the soil or other media in which the plants are grown are above levels that would result in RKN damage in the absence of such applications or use. Soil or media in which the plant is to be grown can be surveyed for the presence of *Meloidogyne* sp. and the composition is applied to the plant part, soil, or media when the *Meloidogyne* sp. are present in the soil or media at a level that can result in reductions in plant growth, yield, water-deficit tolerance, chlorosis, produce quality, and combinations thereof to an untreated control plant. In certain embodiments, the composition is not applied to the plant part, soil, or media when the *Meloidogyne* sp. are present in the soil or media below levels that can result in reductions in plant growth, yield, water-deficit tolerance, chlorosis, produce quality, and combinations thereof to an untreated control plant. Any survey method that provides for a determination of *Meloidogyne* sp. levels that result in plant damage can be used. In certain embodiments, the number of J2 juvenile stage RKN can be determined in the survey (Sorribas F J, Verdejo-Lucas S. *Journal of Nematology.* 1994; 26(4S):731-736. In certain embodiments, survey methods that provide for identification of threshold RKN levels that result in damage to untreated plants can be used to determine if the composition should be applied or if plant parts subjected to such applications should be used. Non-limiting examples of surveys to determine such thresholds have been described and can be adapted for use in the methods described herein (Xing L, Westphal A. *Journal of Nematology.* 2012; 44(2): 127-133; Viaene N M, Abawi G S. *Journal of Nematology.* 1996; 28(4):537-545).

In certain embodiments, the liquid culture medium is prepared from inexpensive and readily available components, including, but not limited to, inorganic salts such as potassium phosphate, magnesium sulfate and the like, carbon sources such as glycerol, methanol, glutamic acid, aspartic acid, succinic acid and the like, and amino acid blends such as peptone, tryptone, and the like. Non-limiting examples of liquid media that can be used include, but are not limited to, ammonium mineral salts (AMS) medium (Whittenbury et al., 1970), Vogel-Bonner (VB) minimal culture medium (Vogel and Bonner, 1956), and LB broth ("Luria-Bertani Broth").

In general, the solid substance that can in certain embodiments be used in the methods and compositions that provide for the efficient growth of *Methylobacterium* can be any suitable solid substance which is insoluble or only partially soluble in water or aqueous solutions. Such suitable solid substances are also non-bacteriocidal or non-bacteriostatic with respect to RKN-active *Methylobacterium* sp. when the solid substances are provided in the liquid culture media. In certain embodiments, such suitable solid substances are also solid substances that are readily obtained in sterile form or rendered sterile. Solid substances used herein can be sterilized by any method that provides for removal of contaminating microorganisms and thus include, but are not limited to, methods such as autoclaving, irradiation, chemical treatment, and any combination thereof. These solid substances include substances of animal, plant, microbial, fungal, or mineral origin, manmade substances, or combinations of substances of animal, plant, microbial, fungal, or mineral origin and manmade substances. In certain embodiments, the solid substances are inanimate solid substances. Inanimate solid substances of animal, plant, microbial, or fungal origin can be obtained from animals, plants, microbes, or fungi that are inviable (i.e. no longer living) or that have been rendered inviable. Diatom shells are thus inanimate solid substances when previously associated diatom algae have been removed or otherwise rendered inviable. Since diatom shells are inanimate solid substances, they are not considered to be photosynthetic organisms or photosynthetic microorganisms. In certain embodiments, solid substances include, but are not limited to, sand, silt, soil, clay, ash, charcoal, diatomaceous earth and other similar minerals, ground glass or glass beads, ground ceramic materials, ceramic beads, bentonite, kaolin, talc, perlite, mica, vermiculite, silicas, quartz powder, montmorillonite, and combinations thereof. In certain embodiments, the solid substance can be a polymer or polymeric beads. Polymers that can be used as a solid substance include, but are not limited to, various polysaccharides such as cellulosic polymers and chitinous polymers which are insoluble or only partially soluble in water or aqueous solutions, agar (i.e. galactans), and combinations thereof. In certain embodiments, the solid substance can be an insoluble or only partially soluble salt crystal. Salt crystals that can be used include, but are not limited to, insoluble or only partially soluble carbonates, chromates, sulfites, phosphates, hydroxides, oxides, and sulfides. In certain embodiments, the solid substance can be a microbial cell, fungal cell, microbial spore, or fungal spore. In certain embodiments, the solid substance can be a microbial cell or microbial spore wherein the microbial cell or microbial spore is not a photosynthetic microorganism. In still other embodiments, the solid substance can be an inactivated (i.e. inviable) microbial cell, fungal cell, microbial spore, or fungal spore. In still other embodiments, the solid substance can be a quiescent (i.e. viable but not actively dividing) microbial cell, fungal cell, microbial spore, or fungal spore. In still other embodiments, the solid substance can be cellular debris of microbial origin. In still other embodiments, the solid substance can be particulate matter from any part of a plant. Plant parts that can be used to obtain the solid substance include, but are not limited to, cobs, husks, hulls, leaves, roots, flowers, stems, barks, seeds, and combinations thereof. Products obtained from processed plant parts including, but not limited to, bagasse, wheat bran, soy grits, crushed seed cake, stover, and the like can also be used. Such plant parts, processed plants, and/or processed plant parts can be milled to obtain the solid material in a particulate form that can be used. In certain embodiments, wood or a wood product including, but not limited to, wood pulp, sawdust, shavings, and the like can be used. In certain embodiments, the solid substance can be a particulate matter from an animal(s), including, but not limited to, bone meal, gelatin, ground or powdered shells, hair, macerated hide, and the like.

In certain embodiments, the solid substance is provided in a particulate form that provides for distribution of the solid substance in the culture media. In certain embodiments, the solid substance is comprised of particle of about 2 microns to about 1000 microns in average length or average diameter. In certain embodiments, the solid substance is comprised of particle of about 1 microns to about 1000 microns in average length or average diameter. In certain embodiments, the solid substance is a particle of about 1, 2, 4, 10, 20, or 40 microns to any of about 100, 200, 500, 750, or 1000 microns in average length or average diameter. Desirable characteristics of particles used in the methods and compositions provided herein include suitable wettability such that the particles can be suspended throughout the media upon agitation.

In certain embodiments, the solid substance is provided in the media as a colloid wherein the continuous phase is a liquid and the dispersed phase is the solid. Suitable solids that can be used to form colloids in liquid media used to grow RKN-active *Methylobacterium* sp. include, but are not limited to, various solids that are referred to as hydrocolloids. Such hydrocolloids used in the media, methods and compositions provided herein can be hydrophilic polymers, of plant, animal, microbial, or synthetic origin. Hydrocolloid polymers used in the methods can contain many hydroxyl groups and/or can be polyelectrolytes. Hydrocolloid polymers used in the compositions and methods provided herein include, but are not limited to, agar, alginate, arabinoxylan, carrageenan, carboxymethylcellulose, cellulose, curdlan, gelatin, gellan, β-glucan, guar gum, gum arabic, locust bean gum, pectin, starch, xanthan gum, and mixtures thereof. In certain embodiments, the colloid used in the media, methods, and compositions provided herein can comprise a hydrocolloid polymer and one or more proteins.

In certain embodiments, the solid substance can be a solid substance that provides for adherent growth of the RKN-active *Methylobacterium* sp. on the solid substance. RKN-active *Methylobacterium* sp. that are adhered to a solid substance are *Methylobacterium* that cannot be substantially removed by simply washing the solid substance with the adherent RKN-active *Methylobacterium* sp. with growth media whereas non-adherent *Methylobacterium* can be substantially removed by washing the solid substance with liquid growth media. In this context, "substantially removed" means that at least about 30%/a, 40%, 50%, 60%, 70%, or 80% the *Methylobacterium* present are removed when the solid substance is washed with three volumes of liquid growth media. Such washing can be effected by a variety of methods including, but not limited to, decanting liquid from a washed solid phase or passing liquid through a solid phase on a filter that permits flow through of bacteria in the liquid. In certain embodiments, the adherent RKN-active *Methylobacterium* sp. that are associated with the solid can include both *Methylobacterium* that are directly attached to the solid and/or *Methylobacterium* that are indirectly attached to the solid substance. *Methylobacterium* that are indirectly attached to the solid substance include, but are not limited to, *Methylobacterium* that are attached to another *Methylobacterium* or to another microorganism that is attached to the solid substance, *Methylobacterium* that are attached to the solid substance by being attached to another substance that is attached to the solid substance, and the like. In certain embodiments, at least 10%, 20%, 30%, 40%, 50%, 60%, 70%, 80%, 90%, 95%, 98%, 99%, 99.5% or 99.9% of the *Methylobacterium* in the fermentation broth, fermentation broth product, or compositions are *Methylobacterium* that are adhered to the solid substance. In certain embodiments, adherent RKN-active *Methylobacterium* sp. can be present on the surface of the solid substance in the fermentation broth, fermentation broth product, or composition at a density of at least about 1 *Methylobacterium*/20 square micrometers, of at least about 1 *Methylobacterium*/10 square micrometers, of at least about 1 *Methylobacterium*/10 square micrometers, of at least about 1 *Methylobacterium*/5 square micrometers, of at least about 1 *Methylobacterium*/2 square micrometers, or of at least about 1 *Methylobacterium*/square micrometer. In certain embodiments, adherent RKN-active *Methylobacterium* sp. can be present on the surface of the solid substance in the fermentation broth, fermentation broth product, or composition at a density of at least about 1 *Methylobacterium*/20 square micrometers to about 1 *Methylobacterium*/square micrometer, of at least about 1 *Methylobacterium*/10 square micrometers to about 1 *Methylobacterium*/square micrometer, of at least about 1 *Methylobacterium*/10 square micrometers to about 1 *Methylobacterium*/square micrometer, of at least about 1 *Methylobacterium*/5 square micrometers to about 1 *Methylobacterium*/square micrometer, or of at least about 1 *Methylobacterium*/2 square micrometers to about 1 *Methylobacterium*/square micrometer. In certain embodiments, adherent RKN-active *Methylobacterium* sp. can be present on the surface of the solid substance in the fermentation broth, fermentation broth product, or composition at a density of at least about 1 *Methylobacterium*/20 square micrometers to about 1 *Methylobacterium*/2 square micrometers, of at least about 1 *Methylobacterium*/10 square micrometers to about 1 *Methylobacterium*/2 square micrometers, of at least about 1 *Methylobacterium*/10 square micrometers to about 1 *Methylobacterium*/2 square micrometers, or of at least about 1 *Methylobacterium*/5 square micrometers to about 1 *Methylobacterium*/2 square micrometers. Biphasic fermentation broths provided herein can comprise a liquid phase that contains non-adherent *Methylobacterium*. In certain embodiments, titers of non-adherent *Methylobacterium* in the liquid phase can be less than about 100,000, 10,000, or 1,000 CFU/ml. In certain embodiments, the RKN-active *Methylobacterium* is selected from the group consisting of *Methylobacterium* NLS0037, a derivative thereof, and a NLS0037-related *Methylobacterium*. In certain embodiments, the RKN-active *Methylobacterium* is selected from the group consisting of *Methylobacterium* NLS0037 and a derivative thereof.

Biphasic culture methods provided can yield fermentation broths with RKN-active *Methylobacterium* sp. at a titer of greater than about $5\times10^8$ colony-forming units per milliliter, at a titer of greater than about $1\times10^9$ colony-forming units per milliliter, at a titer of greater than about $1\times10^{10}$ colony-forming units per milliliter, at a titer of at least about $3\times10^{10}$ colony-forming units per milliliter. In certain embodiments, fermentation broths provided herein can comprise RKN-active *Methylobacterium* sp. at a titer of at least about $5\times10^8$ colony-forming units per milliliter to at least about $3\times10^{10}$ colony-forming units per milliliter, at least about $5\times10^8$ colony-forming units per milliliter to at least about $4\times10^{10}$ colony-forming units per milliliter, or at least about $5\times10^8$ colony-forming units per milliliter to at least about $6\times10^{10}$ colony-forming units per milliliter. In certain embodiments, fermentation broths provided herein can comprise RKN-active *Methylobacterium* sp. at a titer of at least about $1\times10^9$ colony-forming units per milliliter to at least about $3\times10^{10}$ colony-forming units per milliliter, at least about $1\times10^9$ colony-forming units per milliliter to at least about $4\times10^{10}$ colony-forming units per milliliter, or at least about $1\times10^9$ colony-forming units per milliliter to at least about $6\times10^{10}$ colony-forming units per milliliter. In certain embodiments, fermentation broths provided herein will comprise RKN-active *Methylobacterium* sp. at a titer of at least about $1\times10^{10}$ colony-forming units per milliliter to at least about $3\times10^{10}$ colony-forming units per milliliter, at least about $1\times10^{10}$ colony-forming units per milliliter to at least about $4\times10^{10}$ colony-forming units per milliliter, or at least about $1\times10^{10}$ colony-forming units per milliliter to at least about $6\times10^{10}$ colony-forming units per milliliter. In certain embodiments, fermentation broths provided herein will comprise RKN-active *Methylobacterium* sp. at a titer of, at least about $3\times10^{10}$ colony-forming units per milliliter to at least about $4\times10^{10}$ colony-forming units per milliliter, or at least about $3\times10^{10}$ colony-forming units per milliliter to at least about $6\times10^{10}$ colony-forming units per milliliter. In certain embodiments, the RKN-active *Methylobacterium* is selected from the group consisting of *Methylobacterium* NLS0037, a derivative thereof, and a NLS0037-related *Methylobacterium*. In certain embodiments, the RKN-active *Methylobacterium* is selected from the group consisting of *Methylobacterium* NLS0037 and a derivative thereof.

Solid substances with adherent RKN-active *Methylobacterium* sp. can be obtained as fermentation products can be used to make various compositions useful for treating plants or plant parts to inhibit RKN growth and/or reproduction or reduce RKN damage to a plant. Alternatively, compositions provided herein comprising RKN-active *Methylobacterium* sp., solid substances with RKN-active *Methylobacterium* sp. grown thereon, or comprising emulsions with RKN-active *Methylobacterium* sp. grown therein can be used to treat plants or plant parts. Plants, plant parts, and, in particular, plant seeds that have been at least partially coated or coated with the fermentation broth products or compositions comprising RKN-active *Methylobacterium* sp. are thus provided. Also provided are processed plant products that contain the fermentation broth products or compositions with RKN-active *Methylobacterium* sp. or adherent RKN-active *Methylobacterium* sp. Solid substances with adherent RKN-active *Methylobacterium* sp. can be used to make various compositions that are particularly useful for treating plant seeds. Seeds that have been at least partially coated with the fermentation broth products or compositions are thus provided. Also provided are processed seed products, including, but not limited to, meal, flour, feed, and flakes that contain the fermentation broth products or compositions provided herein. In certain embodiments, the processed plant product will be non-regenerable (i.e. will be incapable of developing into a plant). In certain embodiments, the solid substance used in the fermentation product or composition that at least partially coats the plant, plant part, or plant seed or that is contained in the processed plant, plant part, or seed product comprises a solid substance and associated or adherent RKN-active *Methylobacterium* sp. that can be readily identified by comparing a treated and an untreated plant, plant part, plant seed, or processed product thereof. In certain embodiments, the RKN-active *Methylobacterium* is selected from the group consisting of *Methylobacterium* NLS0037, a derivative thereof, and a NLS0037-related *Methylobacterium*. In certain embodiments, the RKN-active *Methylobacterium* is selected from the group consisting of *Methylobacterium* NLS0037 and a derivative thereof.

Compositions useful for treating plants or plant parts that comprise RKN-active *Methylobacterium* sp., a solid substance with adherent RKN-active *Methylobacterium* sp., or comprising emulsions with RKN-active *Methylobacterium* sp. grown therein can also further comprise an agriculturally acceptable adjuvant or an agriculturally acceptable excipient. Such compositions can be in a liquid or dry form. An agriculturally acceptable adjuvant or an agriculturally acceptable excipient is typically an ingredient that does not cause undue phytotoxicity or other adverse effects when exposed to a plant or plant part. In certain embodiments, the solid substance can itself be an agriculturally acceptable adjuvant or an agriculturally acceptable excipient so long as it is not bacteriocidal or bacteriostatic to the *Methylobacterium*. In other embodiments, the composition further comprises at least one of an agriculturally acceptable adjuvant or an agriculturally acceptable excipient. Any of the aforementioned compositions can also further comprise a pesticide. Pesticides used in the composition include, but are not limited to, a nematicide, a fungicide, and a bacteriocide. In certain embodiments, the pesticide used in the composition is a pesticide that does not substantially inhibit growth of the *Methylobacterium*. As *Methylobacterium* are gram negative bacteria, suitable bacteriocides used in the compositions can include, but are not limited to, bacteriocides that exhibit activity against gram positive bacteria but not gram negative bacteria. Compositions provided herein can also comprise a bacteriostatic agent that does not substantially inhibit growth of the *Methylobacterium*. Bacteriostatic agents suitable for use in compositions provided herein include, but are not limited to, those that exhibit activity against gram positive bacteria but not gram negative bacteria. Any of the aforementioned compositions can also be an essentially dry product (i.e. having about 5% or less water content), a mixture of the composition with an emulsion, or a suspension.

Agriculturally acceptable adjuvants used in the compositions that comprise RKN-active *Methylobacterium* sp. include, but are not limited to, components that enhance product efficacy and/or products that enhance ease of product application. Adjuvants that enhance product efficacy can include various wetters/spreaders that promote adhesion to and spreading of the composition on plant parts, stickers that promote adhesion to the plant part, penetrants that can promote contact of the active agent with interior tissues, extenders that increase the half-life of the active agent by inhibiting environmental degradation, and humectants that increase the density or drying time of sprayed compositions. Wetters/spreaders used in the compositions can include, but are not limited to, non-ionic surfactants, anionic surfactants, cationic surfactants, amphoteric surfactants, organo-silicate surfactants, and/or acidified surfactants. Stickers used in the compositions can include, but are not limited to, latex-based substances, terpene/pinolene, and pyrrolidone-based substances. Penetrants can include mineral oil, vegetable oil, esterified vegetable oil, organo-silicate surfactants, and acidified surfactants. Extenders used in the compositions can include, but are not limited to, ammonium sulphate, or menthene-based substances. Humectants used in the compositions can include, but are not limited to, glycerol, propylene glycol, and diethyl glycol. Adjuvants that improve ease of product application include, but are not limited to, acidifying/buffering agents, anti-foaming/de-foaming agents, compatibility agents, drift-reducing agents, dyes, and water conditioners. Anti-foaming/de-foaming agents used in the compositions can include, but are not limited to, dimethopolysiloxane. Compatibility agents used in the compositions can include, but are not limited to, ammonium sulphate. Drift-reducing agents used in the compositions can include, but are not limited to, polyacrylamides, and polysaccharides. Water conditioners used in the compositions can include, but are not limited to, ammonium sulphate.

Methods of treating plants and/or plant parts with the fermentation broths, fermentation broth products, and compositions comprising RKN-active *Methylobacterium* sp. are also provided herein. Treated plants, and treated plant parts obtained therefrom, include, but are not limited to, *Brassica* sp. (e.g., *B. napus, B. rapa, B. juncea*), corn, wheat, rye, rice, alfalfa, rice, rye, sorghum, millet (e.g., pearl millet (*Pennisetum glaucum*), proso millet (*Panicum miliaceum*), foxtail millet (*Setaria italica*), finger millet (*Eleusine coracana*), sunflower, safflower, soybean, tobacco, potato, peanuts, carrot, cotton, sweet potato (*Ipomoea batatus*), cassava, coffee, coconut, pineapple, citrus trees, cocoa, tea, banana, avocado, fig, guava, mango, olive, papaya, cashew, macadamia, almond, sugar beets, sugarcane, strawberry, oats, barley, tomato, lettuce, pepper, green beans, lima beans, peas, cucurbits such as cucumber, cantaloupe, and musk melon, turf, ornamentals, and conifers. Plant parts that are treated include, but are not limited to, leaves, stems, flowers, roots, seeds, fruit, tubers, coleoptiles, and the like. Ornamental plants and plant parts that can be treated include, but are not limited to azalea, hydrangea, hibiscus, roses, tulips, daffodils, petunias, carnation, poinsettia, and chrysanthemum. Seeds or other propagules of any of the aforementioned plants can be treated with the fermentation broths, fermentation broth products, fermentation products, and/or compositions provided herein.

In certain embodiments, plants and/or plant parts are treated by applying the fermentation broths, fermentation broth products, fermentation products, and compositions that comprise RKN-active *Methylobacterium* sp. as a spray. Such spray applications include, but are not limited to, treatments of a single plant part or any combination of plant parts. Spraying can be achieved with any device that will distribute the fermentation broths, fermentation broth products, fermentation products, and compositions to the plant and/or plant part(s). Useful spray devices include a boom sprayer, a hand or backpack sprayer, crop dusters (i.e. aerial spraying), and the like. Spraying devices and or methods providing for application of the fermentation broths, fermentation broth products, fermentation products, and compositions to either one or both of the adaxial surface and/or abaxial surface can also be used. Plants and/or plant parts that are at least partially coated with any of a biphasic fermentation broth, a fermentation broth product, fermentation product, or compositions that comprise a solid substance with RKN-active *Methylobacterium* sp. adhered thereto are also provided herein. Also provided herein are processed plant products that comprise a solid substance with RKN-active *Methylobacterium* sp. adhered thereto.

In certain embodiments, seeds are treated by exposing the seeds to the fermentation broths, fermentation broth products, fermentation products, and compositions that comprise RKN-active *Methylobacterium* sp. Seeds can be treated with the fermentation broths, fermentation broth products, and compositions provided herein by methods including, but not limited to, imbibition, coating, spraying, and the like. Seed treatments can be effected with both continuous and/or a batch seed treaters. In certain embodiments, the coated seeds can be prepared by slurrying seeds with a coating composition containing a fermentation broth, fermentation broth product, or compositions that comprise the solid substance with RKN-active *Methylobacterium* sp. and air drying the resulting product. Air drying can be accomplished at any temperature that is not deleterious to the seed or the *Methylobacterium*, but will typically not be greater than 30 degrees Centigrade. The proportion of coating that comprises a solid substance and RKN-active *Methylobacterium* sp. includes, but is not limited to, a range of 0.1 to 25% by weight of the seed, 0.5 to 5% by weight of the seed, and 0.5 to 2.5% by weight of seed. In certain embodiments, a solid substance used in the seed coating or treatment will have RKN-active *Methylobacterium* sp. adhered thereon. In certain embodiments, a solid substance used in the seed coating or treatment will be associated with RKN-active *Methylobacterium* sp. and will be a fermentation broth, fermentation broth product, or composition obtained by the methods provided herein. Various seed treatment compositions and methods for seed treatment disclosed in U.S. Pat. Nos. 5,106,648, 5,512,069, and 8,181,388 are incorporated herein by reference in their entireties and can be adapted for use with an active agent comprising the fermentation broths, fermentation broth products, or compositions provided herein. In certain embodiments, the composition used to treat the seed can contain agriculturally acceptable excipients that include, but are not limited to, woodflours, clays, activated carbon, diatomaceous earth, fine-grain inorganic solids, calcium carbonate and the like. Clays and inorganic solids that can be used with the fermentation broths, fermentation broth products, or compositions provided herein include, but are not limited to, calcium bentonite, kaolin, china clay, talc, perlite, mica, vermiculite, silicas, quartz powder, montmorillonite and mixtures thereof. Agriculturally acceptable adjuvants that promote sticking to the seed that can be used include, but are not limited to, polyvinyl acetates, polyvinyl acetate copolymers, hydrolyzed polyvinyl acetates, polyvinylpyrrolidone-vinyl acetate copolymer, polyvinyl alcohols, polyvinyl alcohol copolymers, polyvinyl methyl ether, polyvinyl methyl ether-maleic anhydride copolymer, waxes, latex polymers, celluloses including ethylcelluloses and methylcelluloses, hydroxy methylcelluloses, hydroxypropylcellulose, hydroxymethylpropylcelluloses, polyvinyl pyrrolidones, alginates, dextrins, maltodextrins, polysaccharides, fats, oils, proteins, karaya gum, jaguar gum, tragacanth gum, polysaccharide gums, mucilage, gum arabics, shellacs, vinylidene chloride polymers and copolymers, soybean-based protein polymers and copolymers, lignosulfonates, acrylic copolymers, starches, polyvinylacrylates, zeins, gelatin, carboxymethylcellulose, chitosan, polyethylene oxide, acrylamide polymers and copolymers, polyhydroxyethyl acrylate, methylacrylamide monomers, alginate, ethylcellulose, polychloroprene and syrups or mixtures thereof. Other useful agriculturally acceptable adjuvants that can promote coating include, but are not limited to, polymers and copolymers of vinyl acetate, polyvinylpyrrolidone-vinyl acetate copolymer and water-soluble waxes. Various surfactants, dispersants, anticaking-agents, foam-control agents, and dyes disclosed herein and in U.S. Pat. No. 8,181,388 can be adapted for use with an active agent comprising the fermentation broths, fermentation broth products, or compositions provided herein.

Provided herein are compositions that comprise RKN-active *Methylobacterium* sp. that provide control of RKN damage to plants, plant parts, and plants obtained therefrom relative to untreated plants, plant parts, and plants obtained therefrom that have not been exposed to the compositions. In certain embodiments, plant parts, including, but not limited to, a seed, a leaf, a fruit, a stem, a root, a tuber, a pollen grain, or a coleoptile can be treated with the compositions provided herein to inhibit of RKN growth and/or reproduction and/or reduce of RKN damage to a plant. Treatments or applications can include, but are not limited to, spraying, coating, partially coating, immersing, and/or imbibing the plant or plant parts with the compositions provided herein. In certain embodiments, a seed, a leaf, a fruit, a stem, a root, a tuber, or a coleoptile can be immersed and/or imbibed with a liquid, semi-liquid, emulsion, or slurry of a composition provided herein. Such seed immersion or imbibition can be sufficient to provide for inhibition of RKN growth and/or reductions in RKN damage in a treated plant or plant part in comparison to an untreated plant or plant part. Such inhibition of RKN growth and/or reductions in RKN damage includes, but is not limited to inhibition of RKN development and/or reproduction, disruption of RKN feeding behaviors, inhibition of feeding site establishment (e.g., plant giant cell formation), and/or reductions in damage to roots, tubers, or other plant parts relative to untreated plants. In certain embodiments, plant seeds can be immersed and/or imbibed for at least 1, 2, 3, 4, 5, or 6 hours. Such immersion and/or imbibition can, in certain embodiments, be conducted at temperatures that are not deleterious to the plant seed or the *Methylobacterium*. In certain embodiments, the seeds can be treated at about 15 to about 30 degrees Centigrade or at about 20 to about 25 degrees Centigrade. In certain embodiments, seed imbibition and/or immersion can be performed with gentle agitation.

Amounts of the compositions that comprise RKN-active *Methylobacterium* sp. sufficient to provide for a reduction in RKN damage of a plant or plant part can thus be determined by measuring any or all of changes in RKN feeding behavior, RKN growth, RKN reproduction, and/or the adverse effects of RKN feeding in treated plants or plant parts relative to untreated plants or plant parts. Adverse effects of RKN growth and/or reproduction in a plant that can be measured include any type of plant tissue damage or necrosis (e.g., galling of plant parts including but not limited to roots and tubers), any type of plant yield reduction, any reduction in the value of the crop plant product, and/or increases in fungal disease incidence. In certain embodiments, an RKN damage rating scale can be used to assess inhibition of RKN growth and/or reproduction and/or reductions in damage to a plant or plant part. An example of a suitable rating system has been described where the numbers of galls or egg masses per root system are counted and a rating scale where no galls or egg masses=0, 1-2 galls or egg masses=1, 3-10 galls or egg masses=3, 11-30 galls or egg masses=4, and more than 100 galls or egg masses=5 is used to establish a root knot index for galls and for egg masses (Taylor and Sasser, Biology, Identification And Control Of Root-Knot Nematodes, 1978, N.C. State Univ. Dept. Plant Path., and USAID, Raleigh, N.C. 111 pp. Library of Congress Catalog Card Number 77-94505). In certain embodiments, the egg mass index is used to measure RKN control as reproduction is believed to be a more accurate measure of susceptibility to RKN infection. In certain embodiments, determination of the numbers of egg masses can be facilitated by staining RKN infected roots with phloxine B solution. It is also possible to use a rating system scale of 0 to 5 that is based on the percentage of the root system with galls (Hussey and Janssen, Root-knot nematode: *Meloidogyne* species. In: Starr J L, Cook R, Bridge J, editors. Plant Resistance to Parasitic Nematodes. Wallingford, UK: CAB International; 2002. pp. 43-70), where 0=no galling; 1=trace infection with a few small galls; 2=≤25% roots galled; 3=26 to 50%; 4=51 to 75%; and 5=>75% roots galled (Dong et al. J Nematol. 2007 June; 39(2): 169-175).

Compositions provided herein comprising RKN-active *Methylobacterium* sp. are therefore expected to be useful in inhibiting RKN growth and/or reproduction and/or reducing RKN damage in a wide variety of plants, including, but not limited to: *Brassica* sp. (e.g., *B. napus*, *B. rapa*, *B. juncea*), corn, wheat, rye, rice, alfalfa, rice, rye, sorghum, millet (e.g., pearl millet (*Pennisetum glaucum*), proso millet (*Panicum miliaceum*), foxtail millet (*Setaria italica*), finger millet (*Eleusine coracana*), sunflower, safflower, soybean, tobacco, potato, peanuts, carrot, cotton, sweet potato (*Ipomoea batatus*), cassava, coffee, coconut, pineapple, citrus trees, cocoa, tea, banana, avocado, fig, guava, mango, olive, papaya, cashew, macadamia, almond, sugar beets, sugarcane, strawberry, oats, okra, onion, barley, tomato, lettuce, pepper, green beans, lima beans, peas, cucurbits such as cucumber, cantaloupe, and musk melon, turf, ornamentals, and conifers. Compositions provided herein comprising RKN-active *Methylobacterium* sp. are also expected to be useful in inhibiting growth and/or reducing damage caused by *Meloidogyne* arenaria, *Meloidogyne* exigua, *Meloidogyne* hapla, *Meloidogyne* graminis, *Meloidogyne* graminicola, *Meloidogyne* incognita, and *Meloidogyne* javanica.

In certain embodiments, an amount of a composition provided herein that is sufficient to provide for inhibition of RKN damage in a plant or plant part can be a composition with RKN-active *Methylobacterium* sp. at a titer of at least about $1 \times 10^4$ colony-forming units per milliliter, at least about $1 \times 10^5$ colony-forming units per milliliter, at least about $1 \times 10^6$ colony-forming units per milliliter, at least about $5 \times 10^6$ colony-forming units per milliliter, at least about $1 \times 10^7$ colony-forming units per milliliter, at least about $5 \times 10^8$ colony-forming units per milliliter, at least about 1×10⁹ colony-forming units per milliliter, at least about 1×10¹⁰ colony-forming units per milliliter, or at least about 3×10¹⁰ colony-forming units per milliliter. In certain embodiments, an amount of a composition provided herein that is sufficient to provide for inhibition of RKN growth and/or reproduction and/or reduction of RKN damage to a plant or plant part can be a composition with RKN-active *Methylobacterium* sp. at a titer of at least about 1×10⁴ colony-forming units per milliliter, at least about 1×10⁵ colony-forming units per milliliter, about least about 1×10⁶ colony-forming units per milliliter, at least about 5×10⁶ colony-forming units per milliliter, at least about 1×10⁷ colony-forming units per milliliter, or at least about 5×10⁸ colony-forming units per milliliter to at least about 6×10¹⁰, 1×10¹¹, 5×10¹¹, or 1×10¹² colony-forming units per milliliter of a liquid or an emulsion. In certain embodiments, an amount of a composition provided herein that is sufficient to provide for inhibition of RKN growth and/or reproduction and/or reduction of RKN damage to a plant or plant part can be a fermentation broth product with a RKN-active *Methylobacterium* sp. titer of a solid phase of that product is at least about 1×10⁴ colony-forming units per gram, at least about 1×10⁵ colony-forming units per gram, at least about 1×10⁶ colony-forming units per gram, at least about 5×10⁶ colony-forming units per gram, at least about 1×10⁷ colony-forming units per gram, or at least about 5×10⁸ colony-forming units per gram to at least about 6×10¹⁰ colony-forming units of *Methylobacterium* per gram, at least about 1×10¹¹ colony-forming units of *Methylobacterium* per gram, at least about 1×10¹² colony-forming units of *Methylobacterium* per gram, at least about 1×10¹³ colony-forming units of *Methylobacterium* per gram, or at least about 5×10¹³ colony-forming units of *Methylobacterium* per gram of the solid phase. In certain embodiments, an amount of a composition provided herein that is sufficient to provide for inhibition of RKN growth and/or reproduction and/or reduction of RKN damage to a plant or plant part can be a composition with a *Methylobacterium* titer of at least about 1×10⁶ colony-forming units per gram, at least about 5×10⁶ colony-forming units per gram, at least about 1×10⁷ colony-forming units per gram, or at least about 5×10⁸ colony-forming units per gram to at least about 6×10¹⁰ colony-forming units of *Methylobacterium* per gram, at least about 1×10¹¹ colony-forming units of *Methylobacterium* per gram, at least about 1×10¹² colony-forming units of *Methylobacterium* per gram, at least about 1×10¹³ colony-forming units of *Methylobacterium* per gram, or at least about 5×10¹³ colony-forming units of *Methylobacterium* per gram of particles in the composition containing the particles that comprise a solid substance wherein a mono-culture or co-culture of RKN-active *Methylobacterium* sp. is adhered thereto. In certain embodiments, an amount of a composition provided herein that is sufficient to provide for inhibition of RKN growth and/or reproduction and/or reduction of RKN damage to a plant or plant part can be a composition with a *Methylobacterium* titer of at least about 1×10⁶ colony-forming units per mL, at least about 5×10⁶ colony-forming units per mL, at least about 1×10⁷ colony-forming units per mL, or at least about 5×10⁸ colony-forming units per mL to at least about 6×10¹⁰ colony-forming units of *Methylobacterium* per mL in a composition comprising an emulsion wherein a mono-culture or co-culture of a RKN-active *Methylobacterium* sp. adhered to a solid substance is provided therein or grown therein. In certain embodiments, an amount of a composition provided herein that is sufficient to provide for inhibition of RKN growth and/or reproduction and/or reduction of RKN damage to a plant or plant part can be a composition with a *Methylobacterium* titer of at least about 1×10⁶ colony-forming units per mL, at least about 5×10⁶ colony-forming units per mL, at least about 1×10⁷ colony-forming units per mL, or at least about 5×10⁸ colony-forming units per mL to at least about 6×10¹⁰ colony-forming units of *Methylobacterium* per mL of in a composition comprising an emulsion wherein a mono-culture or co-culture of a RKN-active *Methylobacterium* sp. is provided therein or grown therein.

EXAMPLES

The following examples are included to demonstrate certain embodiments. It will be appreciated by those of skill in the art that the techniques disclosed in the following examples represent techniques determined by the Applicants to function well in the practice of the disclosure. However, those of skill in the art should, in light of the instant disclosure, appreciate that many changes can be made in the specific embodiments that are disclosed, while still obtaining like or similar results, without departing from the scope of the invention.

Example 1

Reductions in RKN-mediated Plant Growth and RKN Reproduction

Tomato seeds (*Solanum lycopersicum* variety "Charger" or "Sweet Olive", Johnny's Selected Seeds, Winslow, Me.) in horticubes were treated with 0.25 ml PPFM solution in water at concentration of 1×10⁷ to 1×10⁸ CFU/ml. Control seeds were treated with 0.25 ml water. Plants were grown for approximately two weeks in the greenhouse before transplanting to autoclaved 9:1 sand: soil mixture in pots. Plants were watered as needed with 2.5 g/L Jack's Professional 15-16-17 Peat-Lite Fertilizer. Plants were grown for approximately one additional week before inoculation with *M. hapla* eggs. Inoculum was prepared by diluting the purchased nematode egg solution to concentration of 500 nematodes/ml and adding 5 ml to holes around the roots in each pot (2500 eggs/pot total). Plants were grown approximately 6 additional weeks before harvest.

At harvest, the plant height was measured. Shoots were dried 2-3 days and dry weights were measured. Roots were extracted from the sandy soil, rinsed, and blotted dry. Root fresh weights were measured. The roots were cut into small pieces with scissors and freshly prepared 10% bleach was added. The roots with bleach were vigorously shaken for 3 min, then poured through #40 sieve. The root pieces were rinsed with 10 ml sterile water. The flow through was collected into a 50 ml Falcon tube. The solution was centrifuged at 1000×g for 5 min, and the supernatant carefully decanted until 5 ml of solution containing the eggs remained in the tube. 45 ml of water was added to the remaining egg solution, mixed by inversion, and centrifuged again. This washing process was repeated 2 times. After the final wash, the remaining 5 ml was transferred to a new 15 ml Falcon tube. The volume of this solution was measured and the number of nematode eggs in 10 microliters was counted three times under a dissecting microscope to calculate the total number of nematodes.

Each experiment contained 6 replicates per isolate arranged in 3 blocks. The values obtained from each experiment were normalized to the average values obtained from the control plants. A linear mixed model was fitted using the "lmer" function in the lme4 package (Bates, D., Maechler, M., Bolker, B., & Walker, S. (2014). lme4: Linear mixed-effects models using Eigen and S4. R package version 1.1-7, Available on the http internet site "CRAN.R-project.org/package=lme4") in R (R Core Team (2013). R: A language and environment for statistical computing. R Foundation for Statistical Computing, Vienna, Austria, available on the world wide web internet site "R-project.com"), taking into account the random effects of block. An effect size and p value for each strain was calculated from results of at least three separate experiments in a total of six separate experiments using the inverse variance meta-analysis method (Lipsey, M. W., & Wilson, D. B. (2001). Practical meta-analysis. Thousand Oaks, Calif.: Sage Publications, available on the http internet site mason.gmu.edu/~dwilsonb/ma.html."). Results are shown in Table 1.

TABLE 1

Effects of seed treatments on tomato growth parameters and RKN egg counts.

| Strain | Shoot Weight | | Root Weight | | Total | | | |
|---|---|---|---|---|---|---|---|---|
| | | | | | RKN Eggs | | Eggs/mg Root | |
| | Effect Size | p value | Effect Size | p value | Effect Size | p value | Effect Size | p value |
| NLS0021 | −6% | 0.321 | −8% | 0.226 | −1% | 0.458 | −1% | 0.455 |
| NLS0037 | 14% | 0.060 | 2% | 0.400 | −5% | 0.328 | −13% | 0.094 |
| NLS0068 | −4% | 0.359 | 3% | 0.372 | −10% | 0.218 | −15% | 0.096 |

Each line in the table is the results of inverse variance meta-analysis combining the results of six independent experiments. Each strain was tested in at least three separate experiments.

Treatment with NLS0037 produces a statistically significant increase in shoot weight. Treatments with NLS0037 and NLS0068 significantly reduce the amount of RKN eggs per mg root. Treatment with NLS0021 has no significant effect on tomato growth parameters or RKN eggs counts.

Having illustrated and described the principles of the present disclosure, it should be apparent to persons skilled in the art that the disclosure can be modified in arrangement and detail without departing from such principles.

Although the materials and methods of this disclosure have been described in terms of various embodiments and illustrative examples, it will be apparent to those of skill in the art that variations can be applied to the materials and methods described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A method for reducing *Meloidogyne* sp. damage to a plant that comprises
applying a composition comprising *Methylobacterium* NLS0037 (NRRL B-50941) or a NLS0037-related *Methylobacterium* having a gene encoding a 16S RNA that has at least 100% sequence identity across the entire length of SEQ ID NO: 1, and an agriculturally acceptable excipient and/or an agriculturally acceptable adjuvant to a plant part to obtain a treated plant part; and growing the plant from said treated plant part in the presence of *Meloidogyne* sp., wherein *Meloidogyne* sp. damage to the plant is reduced in comparison to a control plant from a control plant part that is not treated with the *Methylobacterium* and that is grown in the presence of *Meloidogyne* sp.

2. The method of claim 1, wherein the *Methylobacterium* is present on said treated plant part in an amount of at least about $1 \times 10^3$ colony forming units (CFU) of said *Methylobacterium* per treated plant part.

3. The method of claim 1, wherein the *Methylobacterium* is heterologous to the plant part.

4. The method of claim 1, wherein the *Methylobacterium* is *Methylobacterium* NLS0037 (NRRL B-50941) and the plant part is not a tomato plant part.

5. The method of claim 1, wherein the *Meloidogyne* sp. damage is selected from the group consisting of a reduction in plant growth, yield, water-deficit tolerance, chlorosis, produce quality, and combinations thereof.

6. The method of claim 5, wherein the reduction in produce quality is evidenced by a decrease in the number of galls or egg masses in produce obtained from the plant in comparison to the number of galls or egg masses in produce obtained from the control plant.

7. The method of claim 1, wherein the plant part is a seed, leaf, tuber, or root.

8. The method of claim 1, wherein the *Meloidogyne* sp.is selected from the group consisting of *Meloidogyne arenaria*, *Meloidogyne exigua*, *Meloidogyne hapla*, *Meloidogyne graminis*, *Meloidogyne graminicola*, *Meloidogyne incognita*, and *Meloidogyne javanica*.

9. The method of claim 1, wherein the plant part is a *Brassica* sp., corn, wheat, rye, rice, alfalfa, rice, rye, sorghum, millet, soybean, tobacco, potato, peanut, carrot, cotton, coffee, coconut, pineapple, sugar beet, strawberry, oat, barley, tomato, lettuce, pepper, pea, onion, green bean, or cucurbit plant part.

10. The method of claim 1, wherein the method further comprises surveying soil in which the plant is to be grown for the presence of *Meloidogyne* sp. and growing the plant from the treated plant part in the presence of *Meloidogyne* sp. when the *Meloidogyne* sp. are present in the soil at a level that can result in reductions in plant growth, yield, water-deficit tolerance, chlorosis, produce quality, and combinations thereof to an untreated control plant.

11. A method for controlling Root Knot Nematode (RKN) damage to a plant comprising:
(i) applying a composition comprising *Methylobacterium* NLS0037 (NRRL B-50941) or a NLS0037-related *Methylobacterium* having a gene encoding a 16S RNA that has at least 100% sequence identity across the entire length of SEQ ID NO: 1, and an agriculturally acceptable excipient and/or an agriculturally acceptable adjuvant to soil or media where a plant is growing or will be grown; and, (ii) growing a plant, or a plant from seed, in said soil or media and in the presence of RKN, thereby controlling RKN damage to a plant.

12. The method of claim 11, wherein the composition is applied to the soil or media by broadcasting the composition, by drenching the soil with the composition, by depositing the composition in furrow, or any combination thereof.

13. The method of claim 12, wherein the depositing in furrow is performed prior to placing seed in the furrow or at the same time as placing seed in the furrow.

14. The method of claim 11, wherein the composition further comprises a nematicide.

15. The methods of claim 14, wherein the nematicide is selected from the group consisting of an organophosphate, biological, and a carbamate nematicide.

16. The method of claim 11, wherein the method further comprises surveying soil in which the plant or plant from seed is to be grown for the presence of *Meloidogyne* sp. and applying the composition to the soil when the *Meloidogyne* sp. are present in the soil at a level that can result in reductions in plant growth, yield, water-deficit tolerance, chlorosis, produce quality, and combinations thereof to an untreated control plant.

\* \* \* \* \*